United States Patent
Shelton, IV et al.

(10) Patent No.: US 10,729,533 B2
(45) Date of Patent: Aug. 4, 2020

(54) ABSORBABLE POLYMER WITH DRUG ELUTION FOR A MAGNET SPHINCTER ASSIST DEVICE

(71) Applicant: ETHICON LLC, Guaynabo, PR (US)

(72) Inventors: Frederick E. Shelton, IV, Hillsboro, OH (US); Timothy S. Bedard, Kentfield, CA (US)

(73) Assignee: Ethicon LLC, Guaynabo, PR (US)

( * ) Notice: Subject to any disclaimer, the term of this patent is extended or adjusted under 35 U.S.C. 154(b) by 165 days.

(21) Appl. No.: 15/664,514

(22) Filed: Jul. 31, 2017

(65) Prior Publication Data
US 2019/0029800 A1    Jan. 31, 2019

(51) Int. Cl.
| | |
|---|---|
| A61F 2/08 | (2006.01) |
| A61F 2/04 | (2013.01) |
| A61B 17/12 | (2006.01) |
| A61F 2/24 | (2006.01) |
| A61B 17/00 | (2006.01) |
| A61B 17/068 | (2006.01) |
| A61B 17/072 | (2006.01) |
| A61B 17/064 | (2006.01) |

(52) U.S. Cl.
CPC .......... *A61F 2/08* (2013.01); *A61B 17/12099* (2013.01); *A61F 2/04* (2013.01); *A61F 2/243* (2013.01); *A61F 2/2412* (2013.01); *A61B 17/068* (2013.01); *A61B 17/072* (2013.01); *A61B 2017/00827* (2013.01); *A61B 2017/00876* (2013.01); *A61B 2017/0641* (2013.01); *A61B 2017/0647* (2013.01); *A61F 2002/044* (2013.01); *A61F 2002/047* (2013.01); *A61F 2002/0894* (2013.01); *A61F 2210/0004* (2013.01); *A61F 2210/009* (2013.01); *A61F 2220/0016* (2013.01); *A61F 2250/003* (2013.01)

(58) Field of Classification Search
CPC ........................................................ A61F 2/08
See application file for complete search history.

(56) References Cited

U.S. PATENT DOCUMENTS

| | | |
|---|---|---|
| 6,776,791 B1 | 8/2004 | Stallings et al. |
| 7,175,589 B2 | 2/2007 | Deem et al. |
| 7,695,427 B2 | 4/2010 | Kugler et al. |
| 8,070,670 B2 | 12/2011 | Deem et al. |
| 8,734,475 B2 | 5/2014 | Ekvall et al. |

(Continued)

OTHER PUBLICATIONS

U.S. Appl. No. 15/664,665, filed Jul. 31, 2017.

(Continued)

*Primary Examiner* — Matthew W Schall
(74) *Attorney, Agent, or Firm* — Frost Brown Todd LLC

(57) ABSTRACT

An apparatus is configured to be implanted within a biological structure. The apparatus includes a plurality of magnetic elements, an absorbable component, and a non-absorbable component. The plurality of magnetic elements are configured to transition the biological structure between an occluded state and an opened state. The plurality of magnetic elements are biased to encourage the biological structure toward the occluded state. The absorbable component includes a therapeutic substance. The absorbable component is configured to temporarily couple the plurality of magnetic elements with the biological structure when the apparatus is initially implanted within the biological structure.

20 Claims, 26 Drawing Sheets

(56) References Cited

U.S. PATENT DOCUMENTS

| | | | |
|---|---|---|---|
| 10,405,865 B2 | 9/2019 | Shelton, IV et al. | |
| 2002/0120277 A1 | 8/2002 | Hauschild et al. | |
| 2009/0088836 A1 | 4/2009 | Bishop et al. | |
| 2010/0185275 A1 | 7/2010 | Richter et al. | |
| 2011/0087337 A1 | 4/2011 | Forsell | |
| 2011/0106273 A1 | 5/2011 | Belhe et al. | |
| 2011/0190879 A1 | 8/2011 | Bobo et al. | |
| 2012/0184893 A1 | 7/2012 | Thompson et al. | |
| 2013/0150957 A1 | 6/2013 | Weber | |
| 2014/0031951 A1 | 1/2014 | Costello et al. | |
| 2014/0135680 A1* | 5/2014 | Peyman | A61N 5/062 604/20 |
| 2014/0194806 A1 | 7/2014 | Belhe et al. | |
| 2014/0277426 A1 | 9/2014 | Dakin et al. | |
| 2015/0129634 A1 | 5/2015 | Shelton, IV et al. | |
| 2015/0133996 A1 | 5/2015 | Shelton, IV et al. | |
| 2015/0134077 A1 | 5/2015 | Shelton, IV et al. | |
| 2016/0000548 A1 | 1/2016 | Aiden et al. | |
| 2016/0113762 A1 | 4/2016 | Clague et al. | |
| 2016/0361161 A1 | 12/2016 | Braido et al. | |
| 2017/0055986 A1 | 3/2017 | Harris et al. | |
| 2017/0086837 A1 | 3/2017 | Vendely et al. | |
| 2017/0135680 A1 | 5/2017 | Pantages et al. | |
| 2017/0252141 A1* | 9/2017 | Alharmi | A61B 5/6874 |
| 2019/0029688 A1 | 1/2019 | Shelton, IV et al. | |
| 2019/0029794 A1 | 1/2019 | Shelton, IV et al. | |
| 2019/0029795 A1 | 1/2019 | Shelton, IV et al. | |

OTHER PUBLICATIONS

U.S. Appl. No. 15/664,611, filed Jul. 31, 2017.
U.S. Appl. No. 15/664,566, filed Jul. 31, 2017.
U.S. Appl. No. 15/664,464, filed Jul. 31, 2017.

* cited by examiner

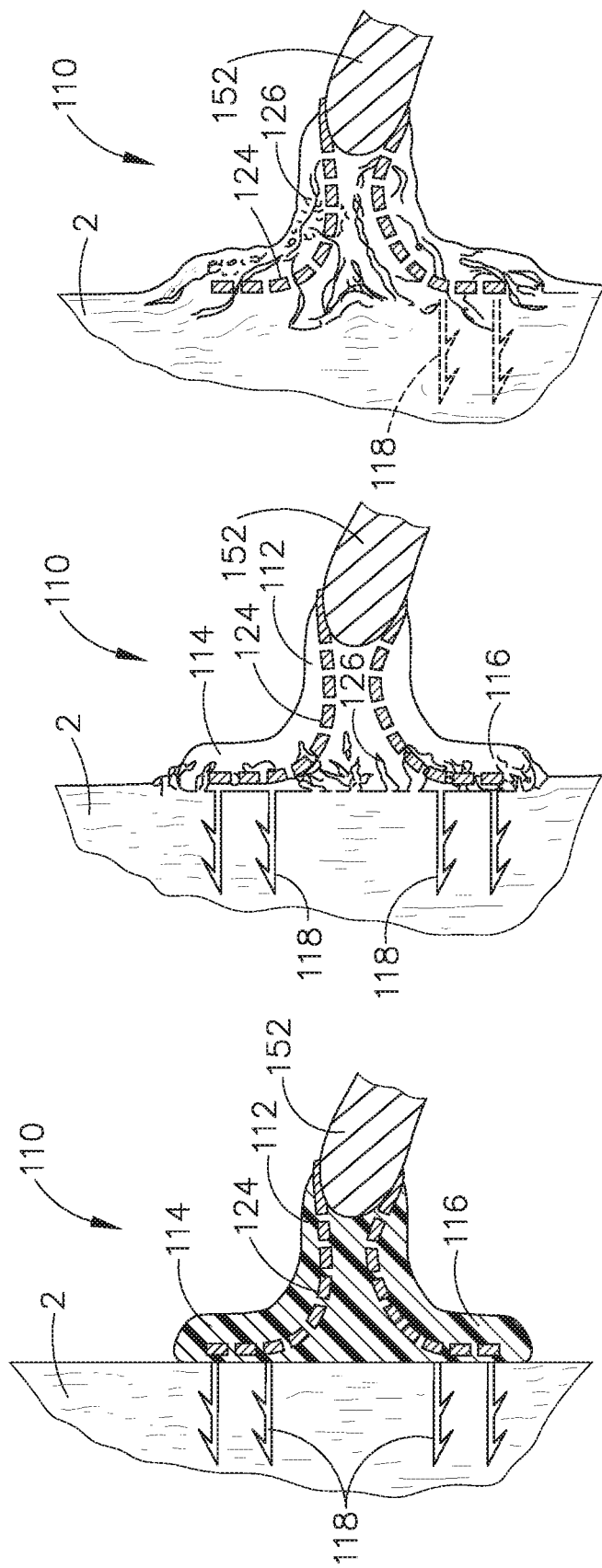

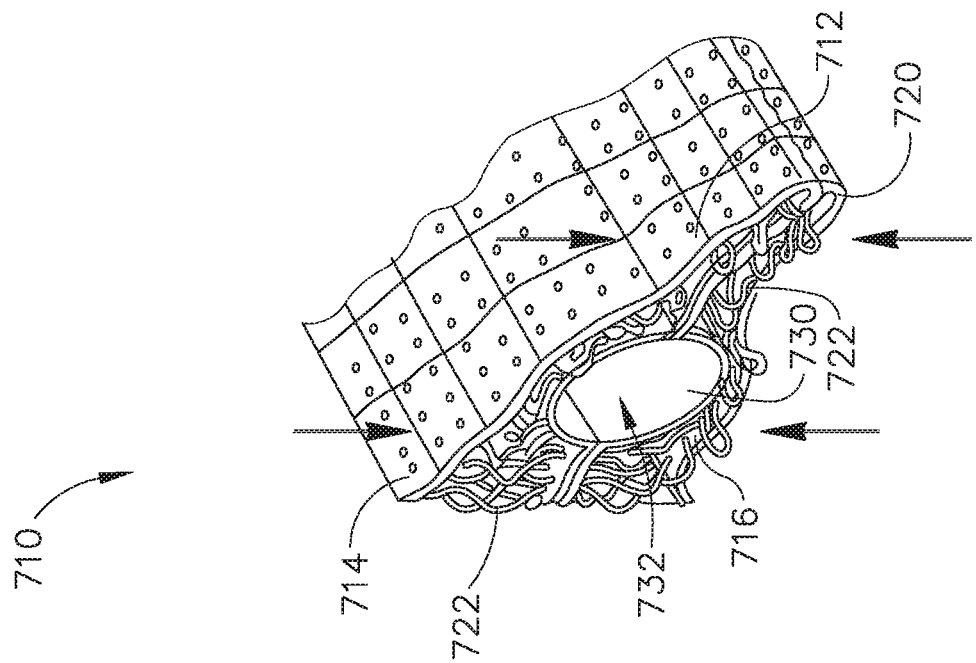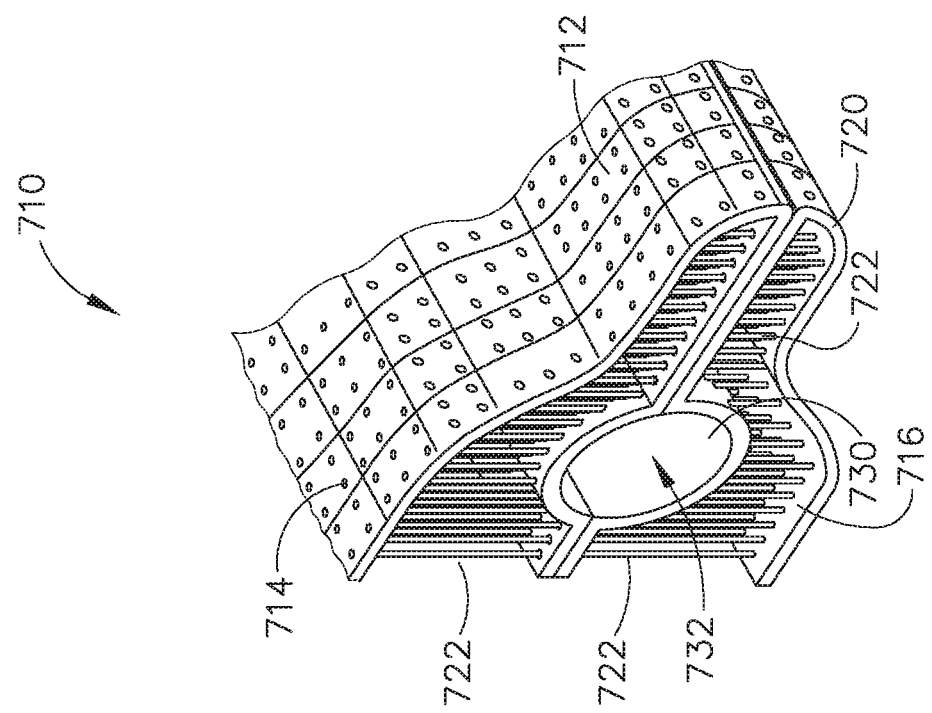

ABSORBABLE POLYMER WITH DRUG ELUTION FOR A MAGNET SPHINCTER ASSIST DEVICE

FIELD OF THE INVENTION

The invention pertains to medical implants and insertion tools for such implants. More specifically, the invention pertains to implants and insertion tools for a biological lumen and/or passageway.

BACKGROUND

In some instances, it may be desirable to place a medical implant within or surrounding a biological lumen/passageway in order to improve or assist the function of, or otherwise affect, the biological lumen/passageway. Examples of such biological lumens/passageways include, but are not limited to, the esophagus, a fallopian tube, a urethra, or a blood vessel. Some biological passages normally function by expanding and contracting actively or passively to regulate the flow of solids, liquids, gasses, or a combination thereof. The ability of a biological passage to expand and contract may be compromised by defects or disease. One merely illustrative example of a condition associated with decreased functionality of a body passage is Gastro Esophageal Reflux Disease (or "GERD"), which effects the esophagus.

A normal, healthy, esophagus is a muscular tube that carries food from the mouth, through the chest cavity and into the upper part of the stomach. A small-valved opening in the esophagus, called the lower esophageal sphincter (or "LES"), regulates the passage of food from the esophagus into the stomach, as well as the passage of acidic fluids and food from the stomach toward the esophagus. The LES may also regulate stomach intra-gastric pressures. A healthy LES may contain pressure of gasses within the stomach at around 10 mm Hg greater than normal intragastrical pressure, thereby impeding acidic gases/fluids from refluxing from the stomach back into the esophagus. When functioning properly, a pressure difference greater than 10 mm Hg may regulate when the LES opens to allow gasses to be vented from the stomach toward the esophagus.

If the LES relaxes, atrophies, or degrades for any reason, the LES may cease functioning properly. Therefore, the LES may fail to sufficiently contain pressure of gasses within the stomach such that acidic contents of the stomach may travel back into the esophagus, resulting in reflux symptoms. Two primary components that control the LES are the intrinsic smooth muscle of the distal esophagus wall and the skeletal muscle of the crural diaphragm or esophageal hiatus. A causation of esophageal reflux, which may be associated with GERD, is relaxation of one or both of the smooth muscle of the distal esophagus wall or the hiatal diaphragm sphincter mechanisms. Chronic or excessive acid reflux exposure may cause esophageal damage. Conventionally, treatment for GERD may involve either open or endoscopic surgical procedures. Some procedures may include a fundoplication that mobilizes of the stomach relative to the lower esophagus, or suturing a pleat of tissue between the LES and the stomach to make the lower esophagus tighter.

Examples of devices and methods that have been developed to treat anatomical lumens by providing sphincter augmentation are described in U.S. Pat. No. 7,175,589, entitled "Methods and Devices for Luminal and Sphincter Augmentation," issued Feb. 13, 2007, the disclosure of which is incorporated by reference herein; U.S. Pat. No. 7,695,427, entitled "Methods and Apparatus for Treating Body Tissue Sphincters and the Like," issued Apr. 13, 2010, the disclosure of which is incorporated by reference herein; U.S. Pat. No. 8,070,670, entitled "Methods and Devices for Luminal and Sphincter Augmentation," issued Dec. 6, 2011, the disclosure of which is incorporated by reference herein; and U.S. Pat. No. 8,734,475, entitled "Medical Implant with Floating Magnets," issued May 27, 2014, the disclosure of which is incorporated by reference herein.

While various kinds and types of lumen implants have been made and used, there is a continuing need in this art for novel implants, insertion tools, applicators, and instruments, and methods of using such implants and instruments which provide improved patient outcomes and other benefits.

SUMMARY OF THE INVENTION

An apparatus is configured to be implanted within a biological structure. The apparatus includes a plurality of magnetic elements, an absorbable component, and a non-absorbable component. The plurality of magnetic elements are configured to transition the biological structure between an occluded state and an opened state. The plurality of magnetic elements are biased to encourage the biological structure toward the occluded state. The absorbable component includes a therapeutic substance. The absorbable component is configured to temporarily couple the plurality of magnetic elements with the biological structure when the apparatus is initially implanted within the biological structure.

An apparatus is configured to be implanted within a biological structure. The apparatus includes a plurality of magnetic elements, an absorbable component, and a non-absorbable component. The plurality of magnetic elements are configured to transition the biological structure between an occluded state and an opened state. The plurality of magnetic elements are biased to encourage the biological structure toward the occluded state. The absorbable component includes a therapeutic substance. The absorbable component is configured to contact the biological structure when the apparatus is initially implanted within the biological structure. The non-absorbable component is configured to initially couple the plurality of magnetic elements with the absorbable component.

An apparatus is configured to be implanted within a biological structure. The apparatus includes an annular retaining assembly and a plurality of magnets. The annular retaining assembly is disposed about a central axis. The annular retaining assembly defines an annular opening. The annular retaining assembly includes an absorbable ring and a non-absorbable ring. The absorbable ring includes a therapeutic substance. The plurality of magnets are configured to transition the biological structure between an occluded state and an opened state. The plurality of magnets are biased to encourage the biological structure toward the occluded state.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 9A depicts a cross-sectional side view, taken along a coronal plane of the body, immediately after the artificial sphincter implant of FIG. 3 has been operatively attached to the interior portion of the LES of the biological passage of FIG. 1;

FIG. 9B depicts a cross-sectional side view, taken along a coronal plane of the body, after a sufficient period of time after the artificial sphincter implant of FIG. 3 has been operatively attached to the interior portion of the LES of the biological passage of FIG. 1 such that there is minor tissue ingrowth around portions of the artificial sphincter implant;

FIG. 9C depicts a cross-sectional side view, taken along a coronal plane of the body, after a sufficient period of time after the artificial sphincter implant of FIG. 3 has been operatively attached to the interior portion of the LES of the biological passage of FIG. 1 such that there is full tissue ingrowth around portions of the artificial sphincter implant;

FIG. 19A depicts a cross-sectional perspective view of an annular retaining assembly of the artificial sphincter implant of FIG. 18 in an un-compressed configuration;

FIG. 19B depicts a cross-sectional perspective view of the annular retaining assembly of FIG. 19A in a compressed configuration;

Figure 1:
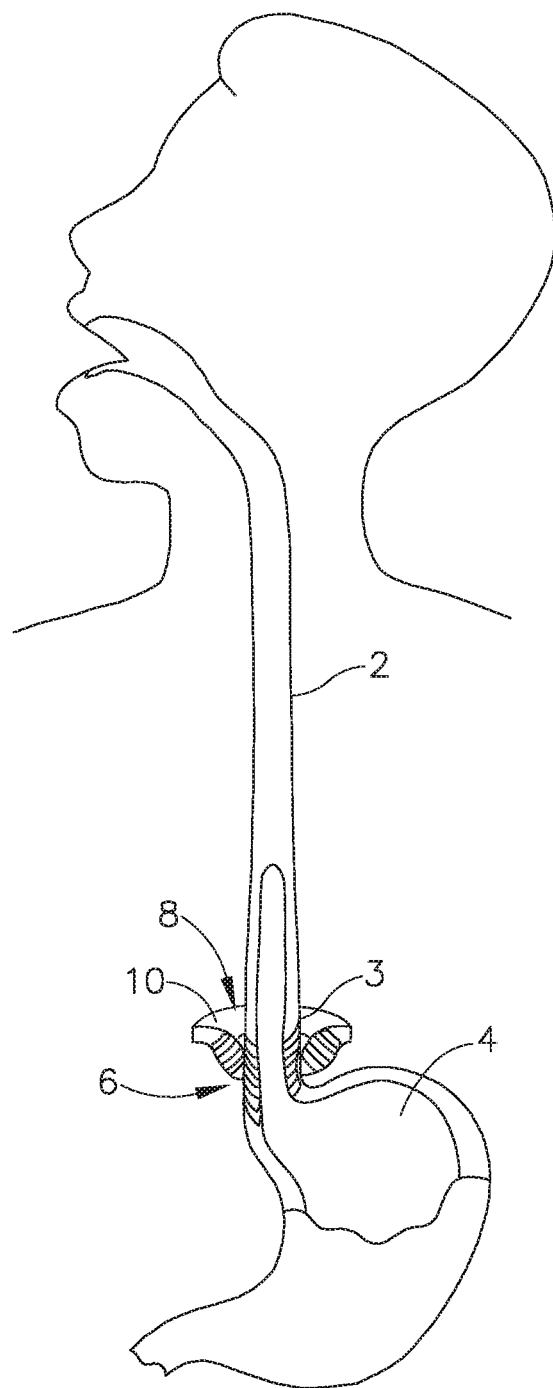
FIG. 1 depicts a cross-sectional side view, taken along a coronal plane of the body, of a biological passage.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview

Figure 2:
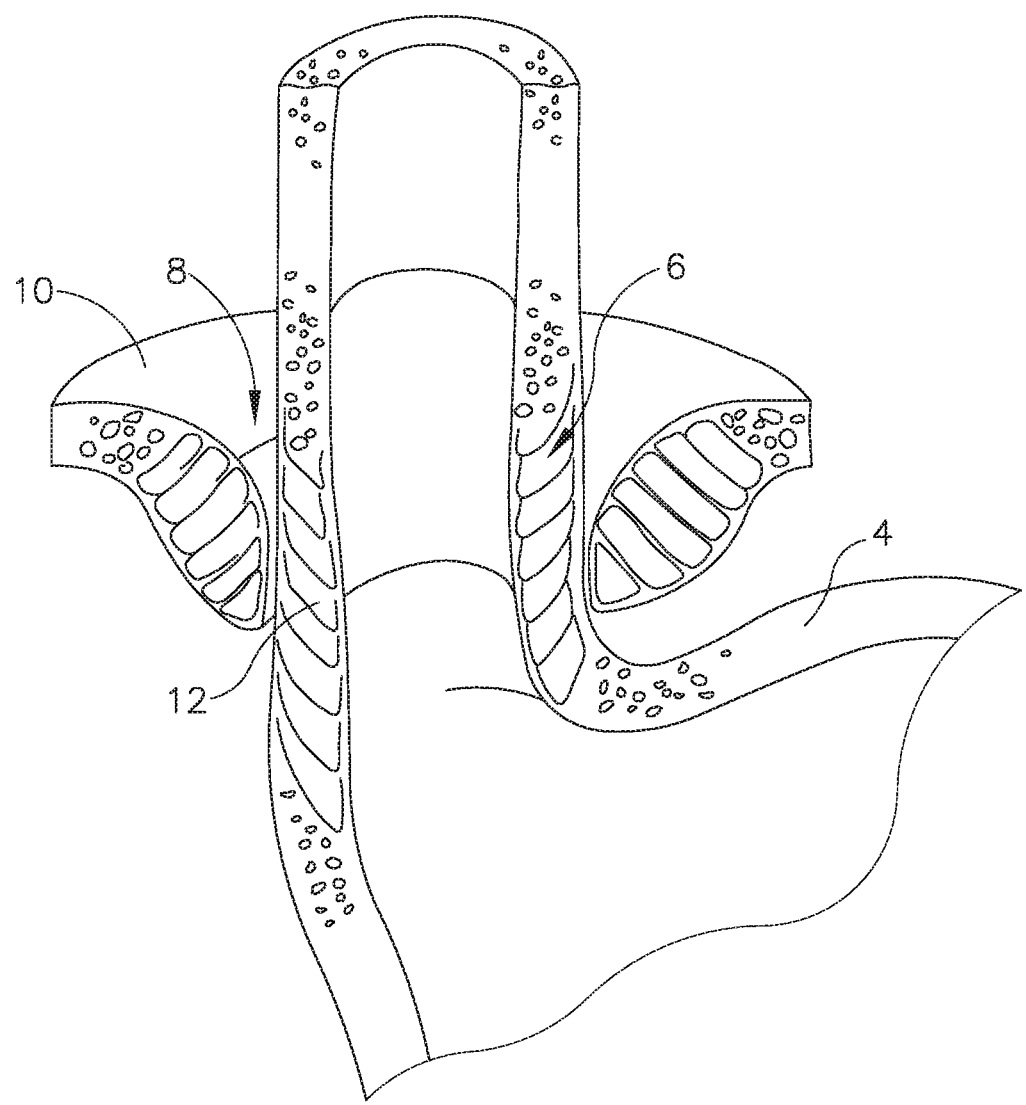
FIG. 2 depicts a cross-sectional isometric view, taken along a coronal plane of the body, of a human esophagogastric junction.

FIGS. 1-2 show selected portions of human anatomy, which includes an esophagus (2) extending from the mouth, through a hiatus (8) defined by a diaphragm (10), and into a stomach (4). Esophagus (2) also includes a distal esophagus (3) and an LES (6). LES (6) is located along distal esophagus (3) adjacent to the junction of esophagus (2) and stomach (4). The portion of LES (6) extending through hiatus (8) is supported by diaphragm (10). When functioning properly, LES (6) is configured to transition between an occluded state and an opened state (as shown in FIG. 2). As best seen in FIG. 2, LES (6) includes a plurality of sling fibers (12). Sling fibers (12) are smooth muscle tissue that may help regulate LES (6) transition between the occluded state and the open state. Hiatus (8) of diaphragm (10) may also help LES (6) transition between the occluded state and the open state.

A healthy LES (6) transitions between the occluded state and the opened state in order to act as a valve. In other words, a healthy LES (6) may transition from the occluded state to the opened state in order to allow solids, liquids, and/or gasses to selectively travel between esophagus (2) and stomach (4). For example, a healthy LES (6) may transition from the occluded state to the opened state to permit a bolus of food to travel from esophagus (2) into stomach (4) during peristalsis; or to vent intra-gastric pressure from stomach (4) toward esophagus (2). Additionally, in the occluded state, a healthy LES (6) may prevent digesting food and acidic fluid from exiting stomach (4) back into esophagus (2).

As mentioned above, if LES (6) ceases functioning properly by prematurely relaxing, and thereby improperly transitioning esophagus (2) from the occluded state to the opened state, undesirable consequences may occur. Examples of such undesirable consequences may include acidic reflux from stomach (4) into esophagus (2), esophageal damage, inflamed or ulcerated mucosa, hiatal hernias, other GERD symptoms, or other undesirable consequences as will be apparent to one having ordinary skill in the art in view of the teachings herein. Therefore, if an individual has an LES (6) that prematurely relaxes, causing improper transitions from the occluded state to the opened state, it may be desirable to insert an implant within or around a malfunctioning LES (6) such that the implant and/or LES (6) may properly transition between the occluded state and the opened state. Several merely illustrative examples of such implants will be described in greater detail below. While in the current illustrative examples, implants are used to replace/reinforce LES (6) of esophagus (2), implants may be used to replace/reinforce any hollow organ sphincter within the body. Nonlimiting examples include the pyloric sphincter, the ileocecal sphincter, the sphincter of Oddi (or Glisson's sphincter), the sphincter urethrae (or urethral sphincter), the internal anal sphincter and external anal sphincter, or the upper esophageal sphincter.

Figure 3:
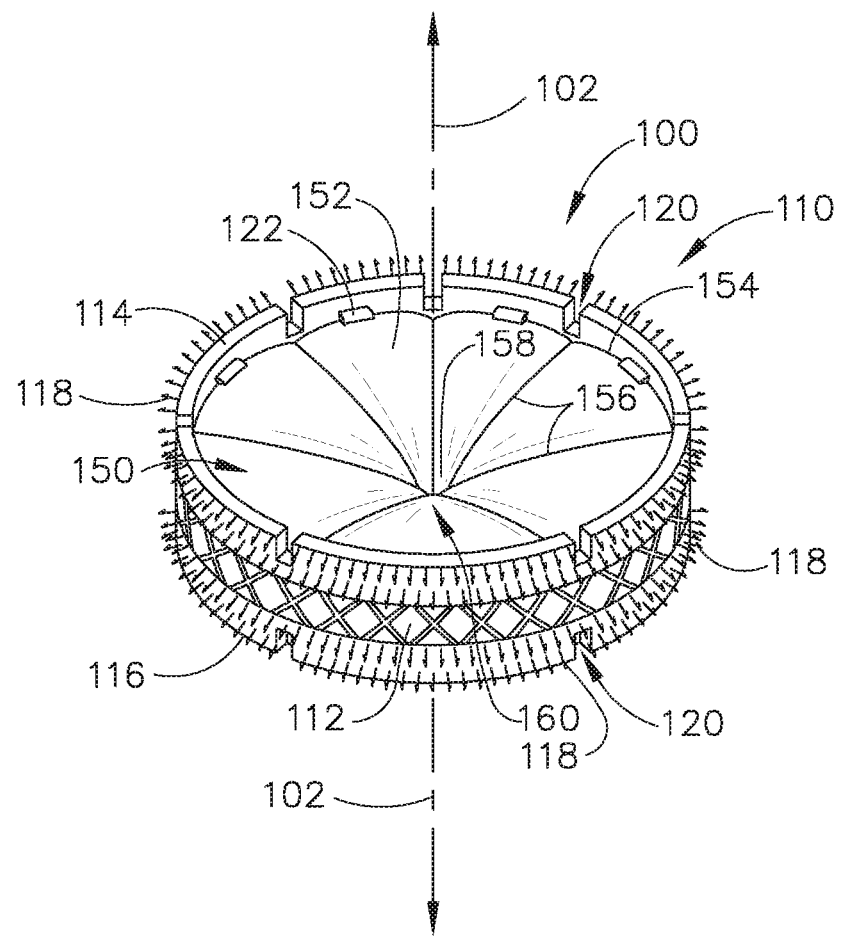
FIG. 3 depicts an isometric view of an exemplary artificial sphincter implant that may be attached to an interior portion of a lower esophageal sphincter (LES) of the biological passage of FIG. 1.

II. Exemplary Internal Artificial Sphincter Implant with Magnetic Internal Seals FIG. 3 shows an exemplary implant (100) that may be attached to the interior of a malfunctioning LES (6) to assist or effectively replace LES (6), thereby allowing esophagus (2) to properly transition between the occluded state and the opened state. In other words, implant (100) may act as an artificial sphincter. While in the current example, implant (100) is used as an artificial sphincter to assist a malfunctioning LES (6), implant (100) may be dimensioned for use as an artificial sphincter within any suitable lumen or passageway for any suitable purpose that would be apparent to one having ordinary skill in the art in view of the teachings herein, even in locations where naturally occurring sphincters are not present.

Implant (100) includes an annular retaining assembly (110) and a valve assembly (150). As will be described in greater detail below, annular retaining assembly (110) is configured to help attach implant (100) within the interior of esophagus (2) such that implant (100) does not substantially move longitudinally relative to esophagus (2) while implanted. As will also be described in greater detail below, valve assembly (150) is configured to assist or effectively replace LES (6) in properly transitioning esophagus (2) between the occluded state and the opened state, thereby helping prevent undesirable consequences of LES (6) prematurely relaxing.

A. Exemplary Annular Retaining Assembly

Annular retaining assembly (110) includes a valve coupling annular body (112), an upper annular flange (114), a lower annular flange (116), a plurality of anchors (118), and coupling members (122). Valve coupling annular body (112) circumferentially extends around a central axis (102). In the current example, valve coupling annular body (112) has a diameter dimensioned for suitable insertion within esophagus (2), in accordance with the description below. However, valve coupling annular body (112) may have any suitable diameter as would be apparent to one having ordinary skill in the art in view of the teachings herein. Coupling members (122) are attached to and extend from an interior facing surface of valve coupling annular body (112). Coupling members (122) also couple with magnetic sectors (152) of valve assembly (150). In other words, coupling members (122) connect magnetic sectors (152) of valve assembly (150) with valve coupling annular body (112) of annular retaining assembly (110).

While in the current example central axis (102) follows a substantially straight line, central axis (102) may follow an approximately central path through a bodily lumen in which implant (100) is being inserted into. Therefore, central axis (102), as well as valve coupling body (112) and annular flanges (114, 116), may not necessarily extend along a substantially straight line, but may extend along a curved profile. A plane perpendicular to, or nearly perpendicular to, central axis (102) may be referred to as an axial plane.

Upper annular flange (114) and lower annular flange (116) extend above and below valve coupling annular body (112), respectively, in a deployed position. As seen in FIG. 8C, a portion of annular flanges (114, 116) directly adjacent to valve coupling annular body (112) may be considered an "outer radial ring;" while a portion of valve coupling annular body (112) radially interior to annular flanges (114, 116) and coupling with magnetic sectors (152) may be considered an "inner radial ring." Upper annular flange (114) and lower annular flange (116) define notches (120) in this example. Notches (120) may promote flexibility of upper annular flange (114) and lower annular flange (116). Additionally, notches (120) may permit the folding of valve coupling annular body (112) and flanges (114, 116) radially toward central axis (102) during initial insertion of implant (100), as will be described in greater detail below.

Annular flanges (114, 116) and valve coupling annular body (112) may be flexible, elastic, and/or moldable in nature such that annular flanges (114, 116) and valve coupling annular body (112) may flex in response to expansion, contraction, or other movement of esophagus (2); such as when esophagus (2) performs peristalsis to move a bolus of food through esophagus (2) toward stomach (4). As esophagus deforms during the wave-like muscle contractions of peristalsis, annular flanges (114, 116) and valve coupling annular body (112) may also deform such that the exterior portions of annular flanges (114, 116) and valve coupling annular body (112) remain in contact with, or substantially fixed relative to, adjacent portions of the interior esophagus (2). Anchors (118) may, at least initially, help promote contact/fixed spatial positioning between the interior esophagus (2) with annular flanges (114, 116) and valve coupling annular body (112).

Valve coupling annular body (112), upper annular flange (114), lower annular flange (116), or any suitable combination thereof may include a material that is inert such that the inert material is biocompatible and resistant to reaction with biochemical solids, liquids, and gasses. Additionally, or alternatively, valve coupling annular body (112), upper annular flange (114), lower annular flange (116), or any suitable combination/portions thereof may include a material that is biocompatible and configured to promote tissue ingrowth. Valve coupling annular body (112), upper annular flange (114), lower annular flange (116), or any suitable combination/portions thereof may include a material that is biocompatible and configured to deteriorate in response to being exposed to biochemical solids, liquids, and/or gasses (otherwise known as absorbable material). Valve coupling annular body (112), upper annular flange (114), lower annular flange (116), or any suitable combination/portions thereof may include an absorbable material also configured to promote tissue ingrowth. Various suitable materials and combinations of materials that may be used will be apparent to one having ordinary skill in the art in view of the teachings herein.

Anchors (118) extend radially away from an exterior surface of both upper annular flange (114) and lower annular flange (116). Therefore, one or more anchors (118) may be presented in or near an axial plane of implant (100). Anchors (118) are configured to at least initially attach implant (100) with an interior portion of esophagus (2). Therefore, anchors (118) are configured to penetrate portions of esophagus (2) to attach implant (100) within the interior of esophagus (2). Anchors (118), valve coupling annular body (112), and/or annular flanges (114, 116) may be coated with a short-term adhesive to promote attaching of implant (100) to esophagus (2), such as cyanoacrylate, fibrin glue, oxidized regenerated cellulose, or any other suitable coating that would be apparent to one having ordinary skill in the art in view of the teachings herein.

As mentioned above, anchors (118) may help promote contact, or otherwise promote a fixed special positioning, between the interior esophagus (2) with annular flanges (114, 116) and valve coupling annular body (112). Additionally, anchors (118) may help valve coupling annular body (112) and flanges (114, 116) remain stationary (or near stationary) in the longitudinal direction defined by central axis (102) of implant (100) as implant (100) experiences external forces. Anchors (118) may also reduce stress on portions of esophagus (2) adjacent to anchors (118). For instance, anchors (118) may help promote stability of valve coupling annular body (112) and flanges (114, 116) in the longitudinal direction defined by central axis (102) when valve coupling annular body (112) and annular flanges (114, 116) are deformed during peristaltic contractions of esophagus (2). In examples where implant (100) is used in biological pathways other than LES (6), anchors (118) may promote stability and reduce stress on biological pathways during circulatory pumping, excretory processes, reproductive processes, or any other suitable physiological process that would be apparent to a person having ordinary skill in the art in view of the teachings herein. Anchors (118) may help reduce the amount of stress experienced by esophagus (2), or any other suitable biological pathway, during deployment of implant (100) as will be described in greater detail below.

Anchors (118) may include an elastic material, a metal, an alloy, a polymer, an inert material, an absorbable material, an absorbable material that promotes tissue growth, any other suitable material that would be apparent to one having ordinary skill in the art in view of the teachings herein, and/or any other suitable combination of the materials mentioned above. Anchors (118) may be made of a material that is less elastic than flanges (114, 116). Anchors (118) may be insert molded into a portion of flanges (112, 114). Additionally, anchors may be wholly or partially embedded in flanges (112, 114).

While anchors (118) are shaped like a barb or quill in the present example, anchors (118) may have any suitable shape that would be apparent to one having ordinary skill in the art in view of the teachings herein. For example, anchors (118) may include a staple, such as a staple that is C-shaped or U-shaped. Anchors (118) may include a catch feature used to resist the withdrawal of anchors (118) from tissue of esophagus (2) such that anchors (118) may be used to pinch, pin, or hook into tissue. In the current example, multiple anchors (118) are used, but it should be understood that a single anchor (118) may be used. In the current example, anchors (118) extend radially away from annular flanges (114, 116). However, anchors (118) may additionally or alternatively extend from valve coupling annular flange (112). As will be described in greater detail below, upper and lower annular flanges (114, 116) may transition from a folded position to a substantially vertical position (as shown in FIG. 3) in order to deploy anchors (118) into surrounding adjacent portions of esophagus (2).

Valve coupling annular body (112), upper annular flange (114), lower annular flange (116), anchors (118), or any suitable combinations/portions therefore may include a coating or therapeutic substance. A coating may include an inert material. The therapeutic substances may include an agent configured to heal tissue from a disease, defect, infection, inflammation, trauma, or any combination thereof. The therapeutic substances may include an agent configured to physically protect tissue from acidic compounds, such as agents that act to neutralize an acidic compound. The therapeutic substances may include a drug, a steroid, an antibiotic, or any other suitable substance that would be apparent to one having ordinary skill in the art in view of the teachings herein. Additionally, therapeutic substances may be embedded in a hollow area, such as a porous portion, of valve coupling annular body (112), upper annular flange (114), lower annular flange (116), or anchors (118). Therapeutic substances may be configured to elute from a portion of the artificial sphincter into the tissue of the biological passageway.

Annular body (112) and flanges (114, 116) may include portions having different flexibilities relative to each other. For instance, some portions may have a low flexibility while other portions have a high flexibility. Low flexibility portions may be thick, short, inelastic, fixed against rotation, shorter, or otherwise noncompliant. High flexibility portions may be thin, lone, elastic, extensible, rotatable, or otherwise compliant. Anchors may be coupled to low and high flexibility portions. Anchors coupled to low flexibility portions may be subject to less stress, less displacement, or both as compared to high flexibility portions. When annular body (112) and flanges (114, 116) expand and contract in response to deformation of esophagus (2), the expansion and contraction may be concentrated in high flexibility portions.

B. Exemplary Valve Assembly

As best seen in FIG. 3, valve assembly (150) includes a plurality of magnetic sectors (152) arranged in a radially extending array around central axis (102). At least a portion of magnetic sectors (152) are positioned within coupling members (122) or an interior of annular retaining assembly (110). Magnetic sectors (152) also define an occludable opening (160) located near central axis (102). The term "occludable opening" is intended to include an opening that may vary in size to selectively permit or inhibit matter from undesirably passing through the opening.

Magnetic sectors (152) form an artificial valve. As will be described in greater detail below, magnetic sectors (152) of valve assembly (150) are configured to assist or effectively replace LES (6) in properly transitioning esophagus (2) between the occluded state and the opened state, which may help prevent undesirable consequences of LES (6) prematurely relaxing. In particular, magnetic sectors (152) utilize a magnetic attraction between adjacent magnetic sectors (152) to bias each other toward the occluded state. Once a sufficient external force is presented, magnetic sectors (152) may bend, flex, or otherwise move away from each other toward the opened state. When in the occluded state, magnetic sectors (152) may inhibit solids, liquids, or gasses from passing undesirably through the interior of implant (100) (e.g., from the stomach (4) to the esophagus (2)). When in the opened state, magnetic sectors (152) may permit solids, liquids, or gasses to pass through the interior of implant (100). Occludable opening (160) may be dimensioned depending on the size of substance passing through occludable opening.

In the present example, each magnetic sector (152) includes a flexible biocompatible magnetic polymer. The flexible magnetic polymer may include a high-coercivity ferromagnetic compound, such as ferric oxide, mixed with a plastic binder, such as PEEK, polypropylene, high density polyethylene, polycarbonate, or any other suitable biocompatible polymer that would be apparent to one having ordinary skill in the art in view of the teachings herein. Magnetic sectors (152) may include expanded polypropylene (EPP), high density polyethylene, or an elastomer (e.g. isoprene of sanoprene) in order to allow elastic deformation or elastic bending of magnetic sectors (152). Various suitable materials that may be used to form magnetic sectors (152) will be apparent to those of ordinary skill in the art in view of the teachings herein.

To make magnetic sectors (152) biocompatible, magnetic sectors (152) may have a coating or encapsulation of a non-absorbable plastic such as PEEK, polypropylene, high density polyethylene, polycarbonate, or any other non-absorbable plastic that would be apparent to one having ordinary skill in the art in view of the teachings herein. Alternatively, the magnetic sectors (152) may have a plating or encapsulation of another non-magnetic material like titanium. Alternatively, magnetic sectors (152) may be coated with a diamond-like carbon (DLC) coating or bioglass which is a commercially available family of bioactive glasses, composed of $SiO_2$, $Na_2O$, $CaO$, and $P_2O_5$ in specific proportions.

While a high-coercivity ferromagnetic compound is used in the present example, any suitable magnetic elements may be used as would be apparent to one having ordinary skill in the art in view of the teachings herein. The magnetic portion of the magnetic polymer may be formed from rare earth magnets, paramagnetic materials, ferromagnets, or any other suitable magnet apparent to one having ordinary skill in the art in view of the teachings herein. Some examples of rare earth magnets include the following: NdFeB (Neodymium Iron Boron), AlNiCo (Aluminum Nickel Cobalt), SmCo (Samarium Cobalt), Strontium ferrite, and barium ferrite. Paramagnetic materials provide a magnetism whereby the materials are attracted by an externally applied magnetic field. Some examples of paramagnetic materials are as follows: [Cr(NH3)6]Br3, K3[Cr(CN)6], K3[MoCl6], K4[V(CN)6], [Mn(NH3)6]Cl2, (NH4)2[Mn(SO4)2]*6H2O, and NH4[Fe(SO4)2]*12H2O. Examples of ferromagnets include iron, nickel, cobalt, manganese, or their compounds (such as CrO2, MnAs, MnBi, EuO, NiO/Fe, Y3Fe5O12).

Figure 4A:
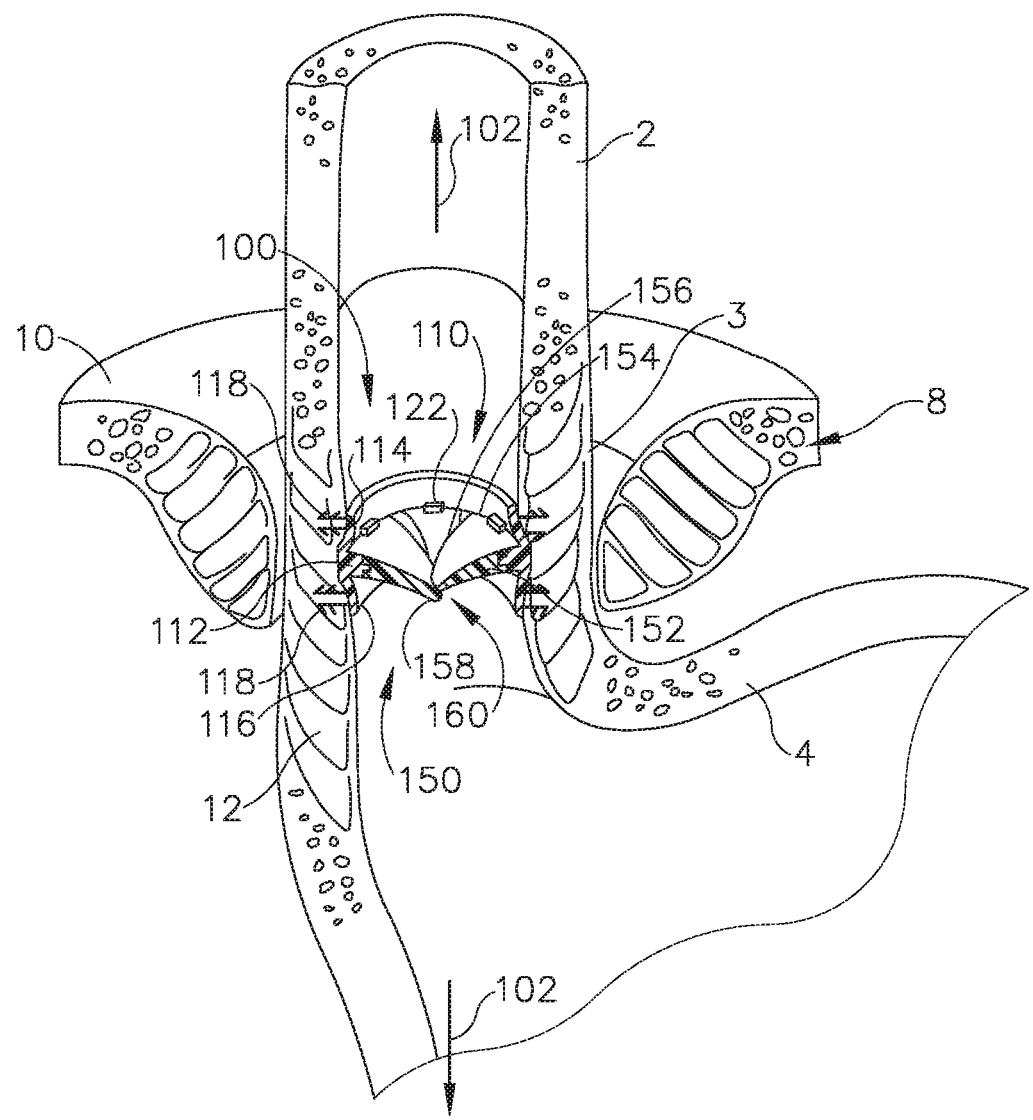
FIG. 4A depicts a cross-sectional isometric view, taken along a coronal plane of the body, where the artificial sphincter implant of FIG. 3 is operatively attached to the interior portion of the LES of the biological passage of FIG. 1, where the artificial sphincter implant is in an occluded configuration.
Figure 4B:
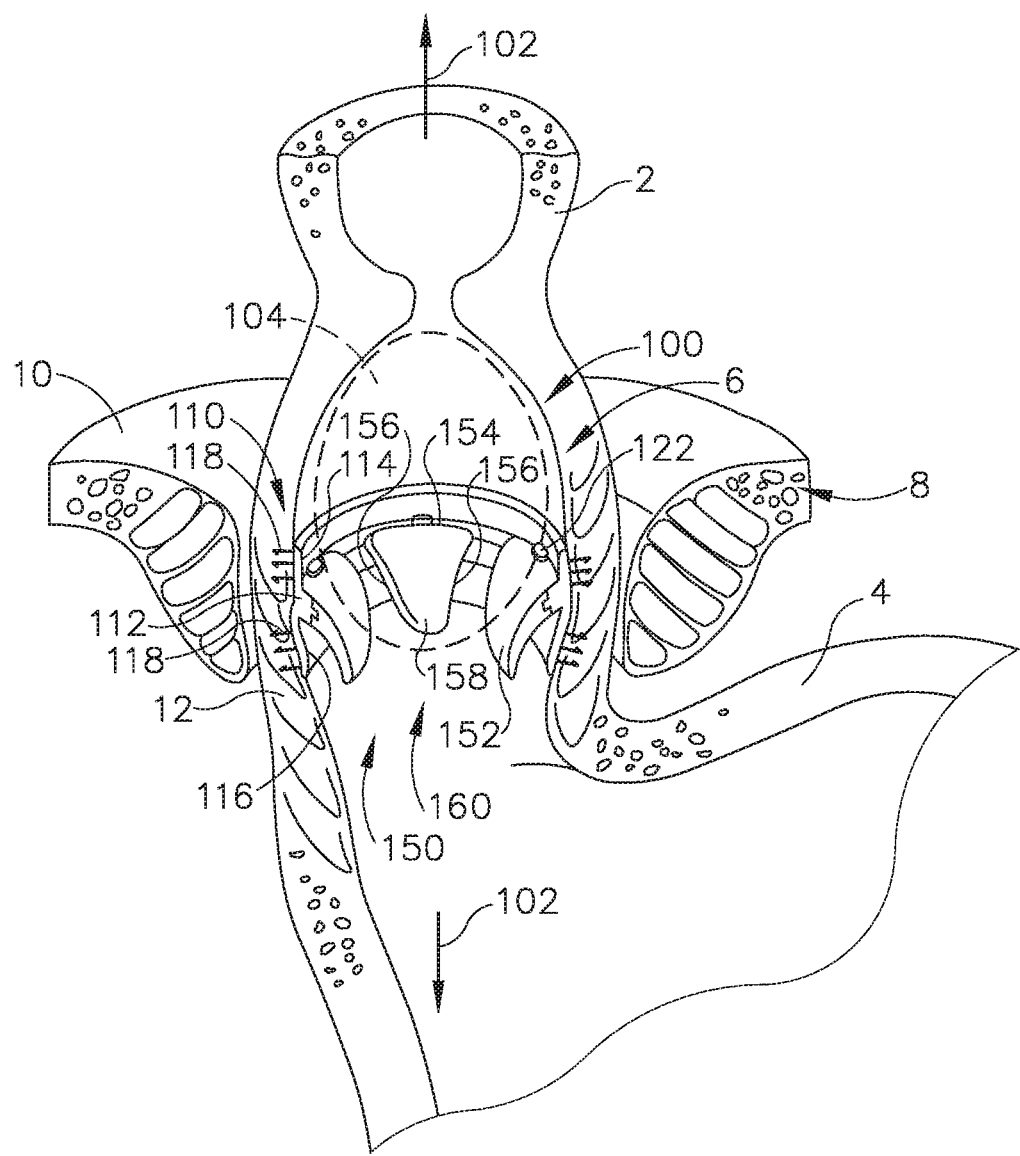
FIG. 4B depicts a cross-sectional isometric view, taken along a coronal plane of the body, where the artificial sphincter implant of FIG. 3 is operatively attached to the interior portion of the LES of the biological passage of FIG. 1, where the artificial sphincter implant is in an opened configuration to accommodate passage of a bolus.

The magnetic poles of magnetic sectors (152) are aligned so that magnetic sectors (152) are magnetically attracted to adjacent magnetic sectors (152). In particular, the magnetic pole alignment of adjacent magnetic sectors (152) bias adjacent magnetic sectors (152) toward each other such that occludable opening (160) is naturally magnetically biased toward the occluded state (as shown in FIG. 4A). Additionally, magnetic sectors (152) may flexibly deform such that occludable opening (160) transitions from the occluded state to an open state (as shown in FIG. 4B) when a sufficient force overcomes the magnetic attraction between adjacent magnetic sectors (152), thereby pushing and flexing magnetic sectors (152) away from each other.

Unlike conventional magnets that have distinct north and south poles, magnetic sectors (152) are flat flexible magnets made from composite materials and may have a traditional through thickness north and south poles, or an alternating north and south poles on the same surface. Of course, magnetic sectors (152) may have any suitable north and south pole arrangement to magnetically attract adjacent magnetic sectors (152) as would be apparent to one having ordinary skill in the art in view of the teachings herein. As one mere example, north and south pole arrangement may have an annular array of north and south pole patterns on the same surface, a radially extending array of north and south pole patterns on the same surface, an arcuate array of north and south pole patterns on the same surface, etc.

Each magnetic sector (152) includes a circumferential perimeter portion (154), two radial perimeter portions (156), and a central tip (158). In the current example, there are four magnetic sectors (152). However, any suitable number of magnetic sectors (152) may be used as would be apparent to one having ordinary skill in the art in view of the teachings herein. Circumferential perimeter portion (154) is dimensioned to complement the interior surface of valve coupling annular body (112) such that circumferential perimeter portions (154) abut or extend into the interior surface of valve coupling annular body (112). In the current example, circumferential perimeter portion (154) of each magnetic sector (152) is equally dimensioned, however this is merely optional. Circumferential perimeter portions (154) may have varying dimensions as would be apparent to one having ordinary skill in the art in view of the teachings herein.

A portion of circumferential perimeter portions (154) may be affixed to coupling members (122) of annular retaining assembly (110). Therefore, each magnetic sector (152) is attached to annular retaining assembly (110) such that at least a portion of each magnetic sector (152) is fixed to annular retaining assembly (110). Annular retaining assembly (110) may act as a mechanical ground for magnetic sectors (152), such that annular retaining assembly (110) allows flexing and bending of magnetic sectors (152) without substantially affecting the spatial positioning of the rest of implant (100) within esophagus (2).

In the current example, coupling members (122) are positioned against the interior surface of valve coupling annular body (112). However, coupling members (122) may be positioned within valve coupling annular body (112) such that circumferential perimeter portions (154) extend within valve coupling annular body (112). Alternatively, circumferential perimeter portions (154) of magnetic sector (152) may extend within the valve coupling annular body (112) such that coupling members (122) are not required. Any suitable portion of each magnetic sector (152) may be affixed to annular retaining assembly (110) as would be apparent to one having ordinary skill in the art in view of the teachings herein.

Radial perimeter portions (156) extend from a terminating end of circumferential perimeter portion (154) toward central axis (102). Radial perimeter portions (156) terminate radially inwardly toward central axis (102) into central tip (158). Radial perimeter portions (156) of directly adjacent magnetic sectors (152) are dimensioned to abut against each other in the occluded state to help form a seal. Additionally, central tips (158) are also dimensioned to abut against each other in the occluded state to also help form a seal. When presented with a sufficient force, radial perimeter portions (156) of directly adjacent magnetic sectors (152) are configured to space away from each other while magnetic sectors (152) flex/bend/deform into the opened state to allow matter to pass through. Additionally, when presented with a sufficient force, central tips (158) are also dimensioned to space away from each other in the opened state to allow matter to pass through.

As best seen in FIG. 3, magnetic sectors (152) of the present example extend toward central axis in a flexed position such that central tips (158) extend downwardly toward stomach (4) as compared to circumferential perimeter portion (154). This flexed position of magnetic sectors (152), while in the occluded state, may allow matter to travel in one direction through valve assembly (150) (i.e., from esophagus (2) to stomach (4)) more easily as compared to a second, opposite, direction (i.e., from stomach (4) to esophagus (2)). This may be, at least in part, caused by the geometry of how central tips (158) interact with other central tips (158). Central tips (158) do not interfere with each other when central tips (158) flex downwardly, as indicative of matter traveling from esophagus (2) toward stomach (4). However, central tips (158) do interfere with each other when central tips (158) flex upwardly, as indicative of matter traveling from stomach (4) toward esophagus (2). This interference may require a larger force to expand occludable opening (160) from the occluded state to the opened state for matter traveling from stomach (4) toward the esophagus (2) as compared to matter traveling from esophagus (2) toward stomach (4).

C. Exemplary Performance of Internal Artificial Sphincter Implant

Figure 4C:
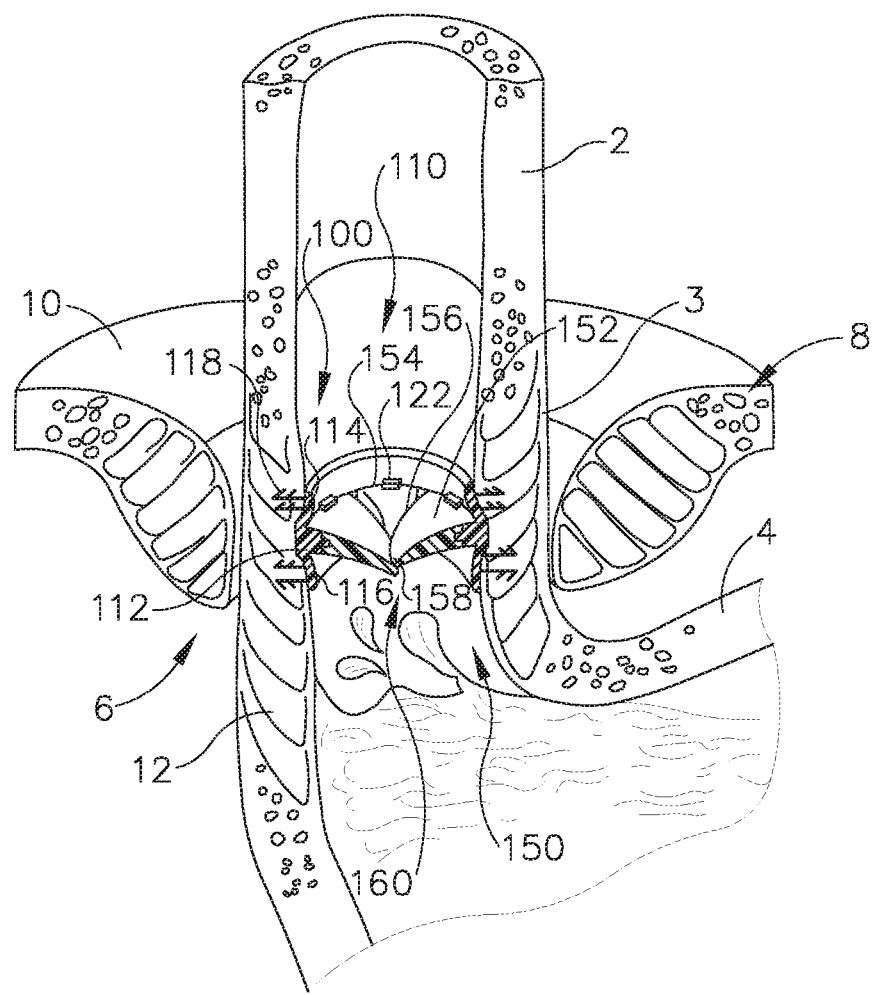
FIG. 4C depicts a cross-sectional isometric view, taken along a coronal plane of the body, where the artificial sphincter implant of FIG. 3 is operatively attached to the interior portion of the LES of the biological passage of FIG. 1, where the artificial sphincter implant is in the occluded configuration after accommodating passage of the bolus of FIG. 4B.
Figure 5:
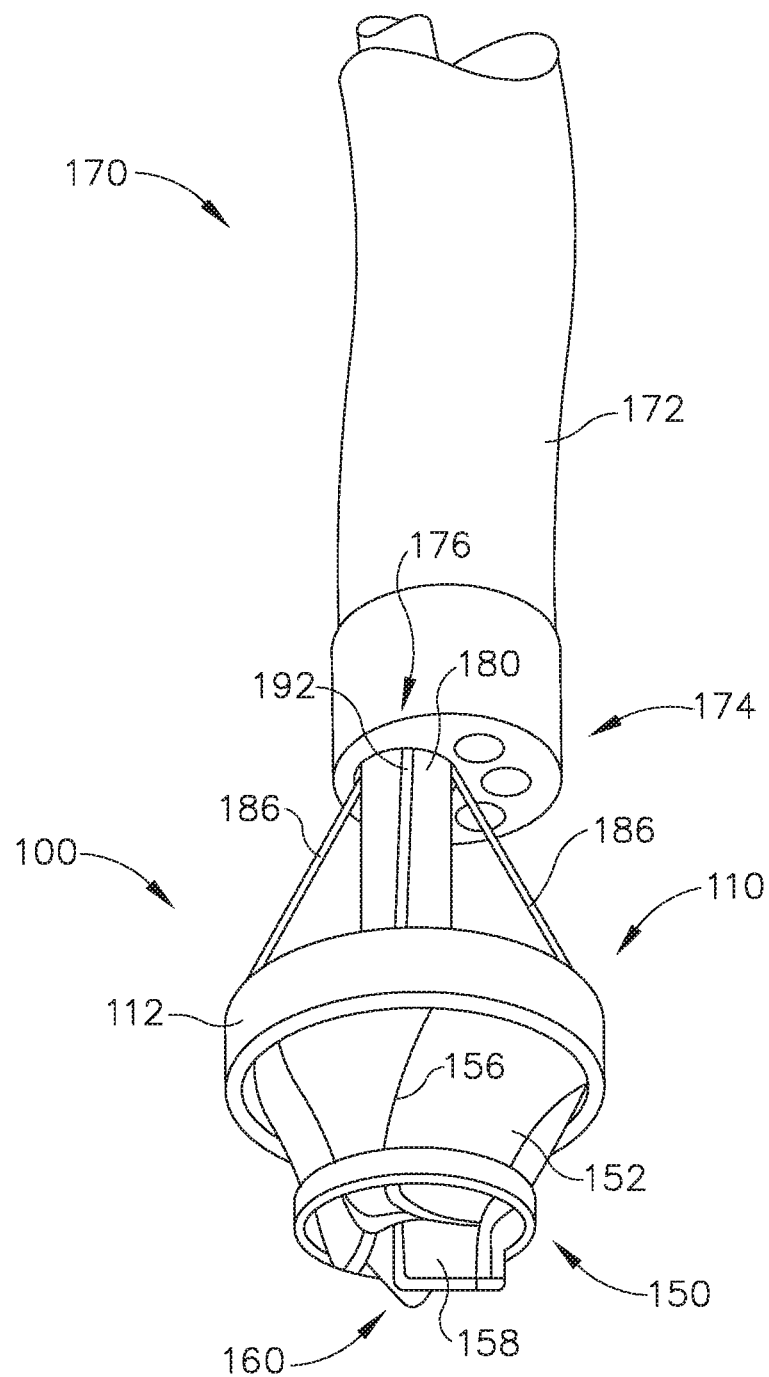
FIG. 5 depicts an isometric view of a deployment assembly attached to the artificial sphincter implant of FIG. 3, with the deployment assembly in a pre-deployed configuration.

FIGS. 4A-4C show an exemplary functioning performance of implant (100) while properly inserted within an interior of esophagus (2), in the region of LES (6). In particular, FIGS. 4A-4C shows valve assembly (150) transitioning from the occluded state, to the opened state, and back to the occluded state. FIG. 4A shows implant (100) properly inserted and implanted into esophagus (2) at the LES (6) region. Annular retaining assembly (110) may remain substantially spatially fixed relative to esophagus (2) along the longitudinal dimension. As described above, the magnetic pole alignment of adjacent magnetic sectors (152) biases magnetic sectors (152) toward each other such that occludable opening (160) is naturally in the occluded state. Therefore, magnetic sectors (152) are in the occluded state such that magnetic sectors (152) may prevent the transfer of solids, fluids, and gasses from exiting stomach (4) and entering esophagus (2). In particular, radial perimeter portions (156) of directly adjacent magnetic sectors (152) may be attracted to each other to promote sufficient contact to provide a sealing effect, while central tips (158) may also be attracted to each other to promote sufficient contact to provide a sealing effect.

As mentioned above, magnetic sectors (152) may flexibly deform such that occludable opening (160) transitions from the occluded state to an opened state when a sufficient force overcomes the magnetic attraction between adjacent magnetic sectors (152), thereby pushing/flexing/deforming magnetic sectors (152) away from each other. FIG. 4B shows esophagus (2) performing a peristalsis procedure where esophagus (2) is pushing a bolus of food (104) toward stomach (4). The bolus of food (104) provides a sufficient force to overcome the magnetic biasing forces and to transition occludable opening (160) into the opened state such that the bolus of food (104) may pass from esophagus (2), through implant (100), and into stomach (4). Therefore, radial perimeter portions (156) and central tips (158) space away from each other to allow bolus of food (104) to pass from esophagus (2) into stomach (4).

Once a sufficient force is no longer present (i.e., after bolus of food (104) passes through implant (100)), the magnetic attraction between adjacent magnetic sectors (152) will bias and flex magnetic sectors (152) back into the position associated with where occludable opening (160) in the occluded state. As shown in FIG. 4C, once bolus of food (104) passes from esophagus (2) into stomach (4), radial perimeter portion (156) and central tips (158) return to their natural position due to the magnetic attraction between adjacent magnetic sectors (152) to help form a seal, thereby transitioning occludable opening (160) from the opened state back to the occluded state.

It should be understood that magnetic sectors (152) may flex upwardly such that occludable opening (160) transitions from the occluded state to the opened state. For instance, a suitable force may be provided by intra-gastric pressure from stomach (4), such that the intra-gastric pressure may be vented through implant (100) and esophagus (2) (e.g., to allow a belch). While magnetic sectors (152) may permit such desirable venting of gas from stomach (4) through esophagus (2), magnetic sectors (152) may still prevent undesirable communication of liquids and/or solids (e.g., acid, chyme, etc.) from stomach (4) into esophagus (2).

III. Exemplary Deployment Assembly for Internal Artificial Sphincter Implant

FIGS. 5-8B show a deployment assembly (170) that may be used to insert and deploy implant (100) within esophagus (2). As shown between FIGS. 6A-6C, and as will be described in greater detail below, deployment assembly (170) is configured to insert implant (100) through the patient's mouth and within esophagus (2) in a first pre-deployed position (FIG. 6A) in order to properly position implant (100) along the profile of esophagus (2), to radially expand implant (100) to a second pre-deployed position (FIG. 6B) in order to initially contact the interior wall of esophagus (2), and transition implant (100) to a deployed position (FIG. 6C) in order to engage anchors (118) with esophagus (2), thereby substantially fixing annular retaining assembly (110) within esophagus (2).

Figure 6A:
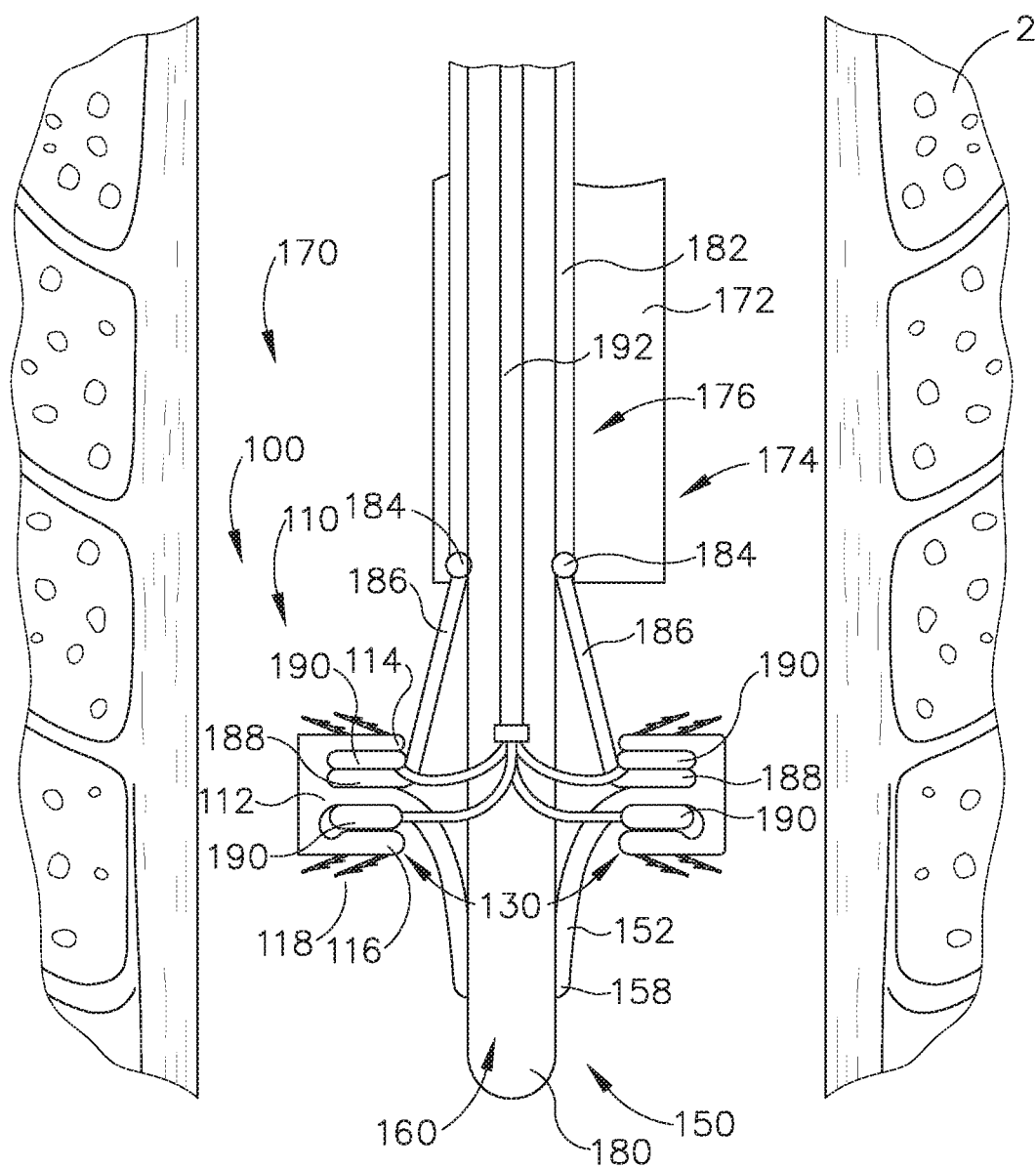
FIG. 6A depicts a cross-sectional side view, taken along a coronal plane of the body, where the deployment assembly of FIG. 5 is inserted into an esophagus of the biological passage of FIG. 1, where the deployment assembly and the artificial sphincter implant of FIG. 3 are in the pre-deployed position.
Figure 6B:
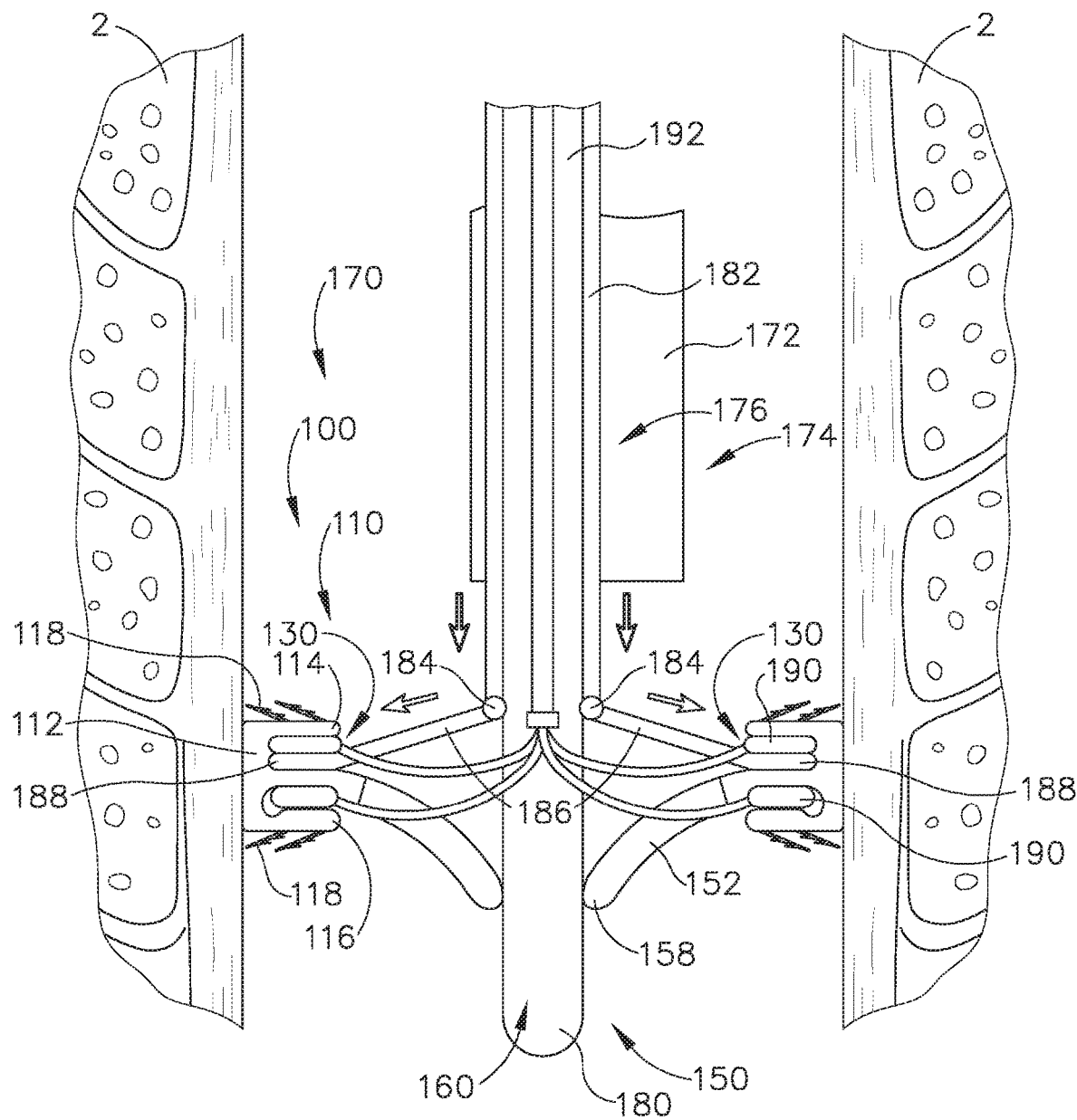
FIG. 6B depicts a cross-sectional side view, taken along a coronal plane of the body, where the deployment assembly of FIG. 5 is inserted into the esophagus of the biological passage of FIG. 1, where the deployment assembly has expanded the artificial sphincter implant of FIG. 3 into a first deployed position.

Deployment assembly (170) includes a flexible endoscope (172) terminating at a distal end (174). Flexible endoscope (172) is dimensioned and sufficiently flexible to be inserted through the mouth of a patient and within esophagus (2). Flexible endoscope (172) also defines a working channel (176) that extends through distal end (174). Working channel (176) is dimensioned to slidably house a sheath (182) which surrounds a shaft (180). As will be described in greater detail below, the sheath (182) may slide relative to flexible endoscope (172) to radially expand implant (100) from the first pre-deployed position (FIG. 6A) to the second pre-deployed position (FIG. 6B).

The distal end of sheath (182) is coupled to a plurality of biased pivot members (184). Biased pivot members (184) are each coupled to a respective rotatable arm (186) extending distally from sheath (182). Therefore, biased pivot members (184) couple rotatable arms (186) to sheath (182). Rotatable arms (186) are configured to pivot relative to sheath (182) about biased pivot members (184). Each rotatable arm (186) also includes a distal end (188). Distal ends (188) of rotatable arms (186) are selectively coupled with implant (100) such that movement of distal ends (188) cause movement of implant (100). In particular, each distal end (188) is housed within a respective pocket (130) temporarily defined by flanges (114, 116) and valve coupling annular body (112) while implant (100) is in the first and second pre-deployed positions. Distal ends (188) of rotatable arms (186) are selectively coupled with implant (100) via an interference fit within corresponding pockets (130). Of course, distal ends (188) of rotatable arms (186) may be selectively coupled with implant (100) via any suitable means that would be apparent to one having ordinary skill in the art in view of the teachings herein. Any suitable number of rotatable arms (186) may be incorporated into deployment assembly (170) as would be apparent to one having ordinary skill in the art in view of the teachings herein.

As mentioned above, rotatable arms (186) are configured to pivot about biased pivot members (184) relative to sheath (182). As also mentioned above, sheath (182) may slide relative to flexible endoscope (172) to radially expand implant (100). In particular, biased pivot members (184) may bias rotatable arms (186) to an outwardly extending position (as shown in FIG. 6B). However, sheath (182) may be initially located within working channel (176) such that rotatable arms (186) are also at least partially housed within working channel (176). Therefore, while biased pivot member (184) may attempt to urge rotatable arms (186) to the outwardly extending position, working channel (176) may constrain rotatable arms (186) to an inwardly extending position (as shown in FIG. 6A). In other words, while biased pivot member (184) may naturally urge rotatable arms (186) to an outwardly extending position, working channel (176) may force rotatable arms (186) into the inwardly extending position if rotatable arms (186) are partially located within working channel (176). Because rotatable arms (186) are temporarily coupled with a flexible, elastic, and/or moldable implant (100) during the first and second pre-deployed positions, the location of rotatable arms (186) relative to sheath (182) (i.e. the inwardly extending position of the outwardly extending position) may determine whether implant (100) is radially contracted in the first pre-deployed position or radially expanded in the second pre-deployed position.

If sheath (182) is in a location such that a portion of rotatable arms (186) is housed within working channel (176), rotatable arms (186) may be in the inwardly extending position, forcing implant (100) in the first pre-deployed position. Alternatively, if sheath is translated distally to a location such that rotatable arms (186) are not housed within working channel (176), biased pivot members (184) may pivot rotatable arms (186) to the outwardly extending position, forcing implant (100) in the second pre-deployed position. Therefore, sheath (182) may slide relative to flexible endoscope (172) in order to radially expand implant (100) within esophagus (2) from the first pre-deployed position to the second pre-deployed position. Any suitable number of rotatable arms (186) may be used as would be apparent to one having ordinary skill in the art in view of the teachings herein.

Shaft (180) extends distally through working channel (176) and distal end (174) along central axis (102) within implant (100) such that central tips (158) rest against shaft (180) when implant (100) is attached to deployment assembly (170). A plurality of inflation lines (192) extend along an exterior of shaft (180). The proximal ends (not shown) of inflation lines (192) may be in fluid communication with any suitable fluid source, such as a syringe, pump, etc. Each inflation line (192) is also in fluid communication with an inflatable member (190). As will be described in greater detail below inflation lines (192) may communicate fluid from fluid source (not shown) into inflatable member (190) to expand inflatable member (190). Inflatable members (190) are housed with pockets (130) temporarily defined by flanges (114, 116) folded radially inwardly toward valve coupling annular body (112). As mentioned above, pocket (130) is defined while implant (100) is in the first and second pre-deployed positions.

When flanges (114, 116) are folded radially inwardly to define pockets (130), anchors (118) are in a disengaged position. When in the disengaged position, anchors (118) are angled to help prevent accidental contact between anchors (118) and the interior of esophagus (2). Therefore, it may be easier to insert implant (100) within esophagus (2) with anchors (118) in the disengaged position such that anchors (118) do not accidentally snag a portion of esophagus (2) during insertion of implant (100). Conversely, anchors (118) may be presented to penetrate, or otherwise couple with, esophagus (2) in an engaged position. As will be described in greater detail below, inflatable members (190) are configured to selectively expand in order to drive implant (100) from the second pre-deployed position into the deployed position such that flanges (114, 116) fold radially outwardly, causing anchors (118) to transition from the disengaged position to the engaged position. Anchors (118) may penetrate, or otherwise couple with, esophagus (2) in the engaged position.

Alternatively, a sheath may cover annular body (112) and flanges (114, 116) to keep anchors (118) in the disengaged position. The sheath may prevent anchors (118) from extending radially away from flanges (114, 116). The sheath may then be removed to encourage anchors (118) to transition to the engaged position.

FIGS. 6A-8C show an exemplary deployment of implant (100) where deployment assembly (170) is used to insert and deploy implant (100) within esophagus (2). First, as best seen in FIG. 6A, biased pivot members (184) are within working channel (176) such that portions of rotatable arms (186) are also located within working channel (176). As mentioned above, flanges (114, 116) are folded radially inwardly to define pockets (130), with which distal ends (188) of rotatable arms (186) are coupled. Therefore, working channel (176) constrains rotatable arms (186) in the inwardly extending position as described above such that implant (100) is in the first pre-deployed position. Because annular retaining assembly (110) of implant (100) is coupled to deployment assembly (170) and folded radially inwardly in the first pre-deployed position, an operator may insert deployment assembly (170) and implant (100) through the mouth and within esophagus (2) until implant (100) is located adjacent to the desired implant location within esophagus (2) (e.g., in the region of LES (6)).

As best seen in FIGS. 6B and 7A, the operator may then slide sheath (182) distally through working channel (176) such that rotatable arms (186) are no longer partially constrained within working channel (176). Because working channel (176) is no longer constraining rotatable arms (186), biased pivot members (184) urge rotatable arms (186) to pivot about biased pivot members (184) from the inwardly extending position to the outwardly extending position. Because distal ends (188) of rotatable arms (186) are still coupled within implant (100) via pockets (130), and because annular flanges (114, 116) and valve coupling annular body (112) are flexible, elastic, moldable, and/or malleable, pivoting of rotatable arms (186) radially expands annular retaining assembly (110) from the first pre-deployed position to the second pre-deployed position. Therefore, valve coupling annular body (112) abuts against the interior wall of esophagus (2). At this point, flanges (114, 116) are still folded radially inwardly relative to valve coupling annular body (112), thereby maintaining anchors (118) in the disengaged position.

Figure 6C:
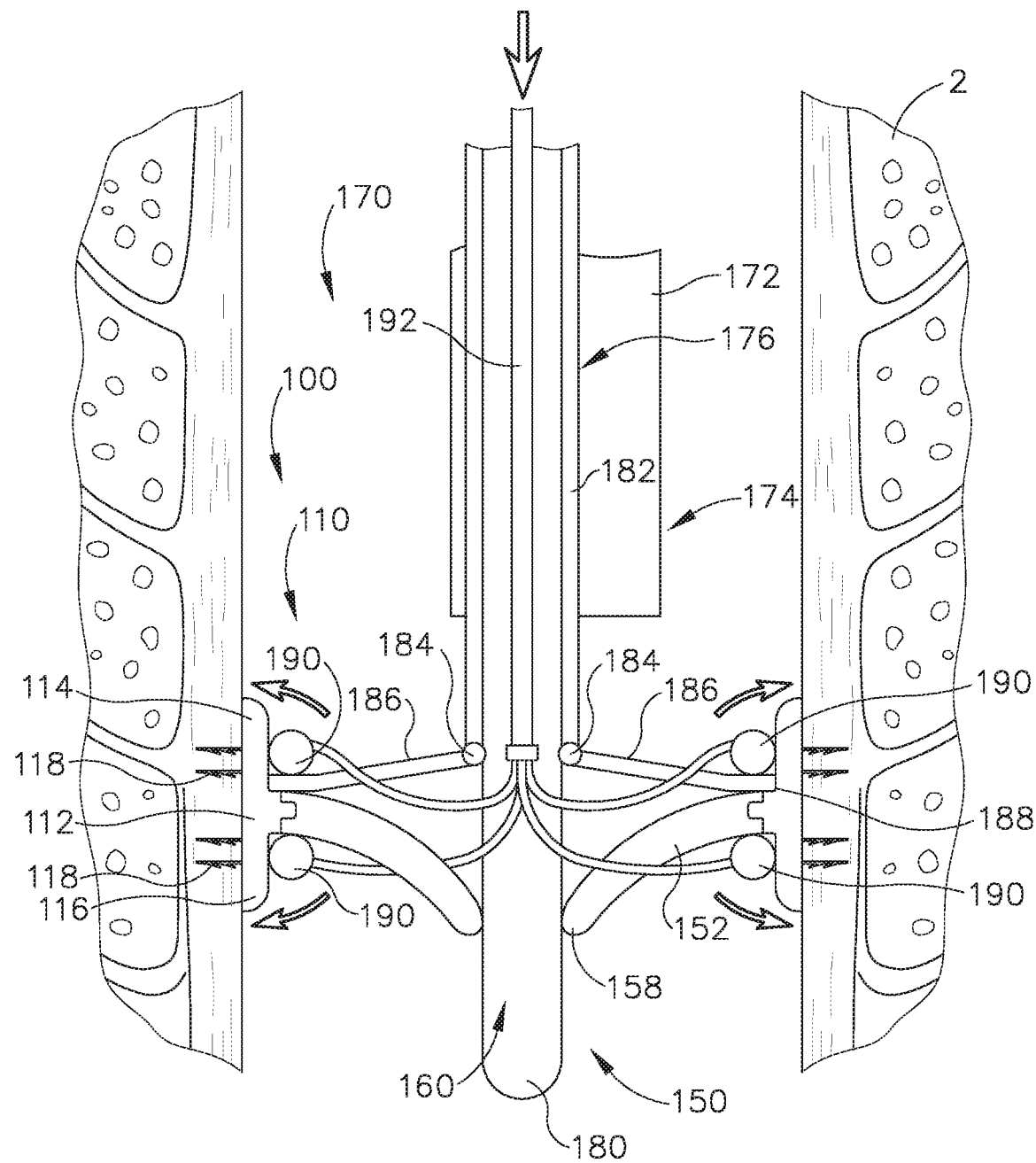
FIG. 6C depicts a cross-sectional side view, taken along a coronal plane of the body, where the deployment assembly of FIG. 5 is inserted into the esophagus of the biological passage of FIG. 1, where the deployment assembly has expanded the artificial sphincter implant of FIG. 3 into a second deployed position.

With implant (100) placed in the desired location of esophagus (2) (e.g., within the region of LES (6)), the operator may then substantially fix annular retaining assembly (110) within esophagus (2) by transitioning implant (100) from the second pre-deployed position to the deployed position. To that end, as best seen between FIGS. 6B-6C and 8A-8C, the operator may drive fluid from a fluid source (not shown), through inflation lines (192) and into inflatable members (190) such that inflatable members (190) expand from a deflated configuration (as shown in FIGS. 6B and 8A) into a partially inflated configuration (as shown in FIG. 8B), and finally into a completely inflated configuration (as shown in FIGS. 6C and 8C).

Figure 7:
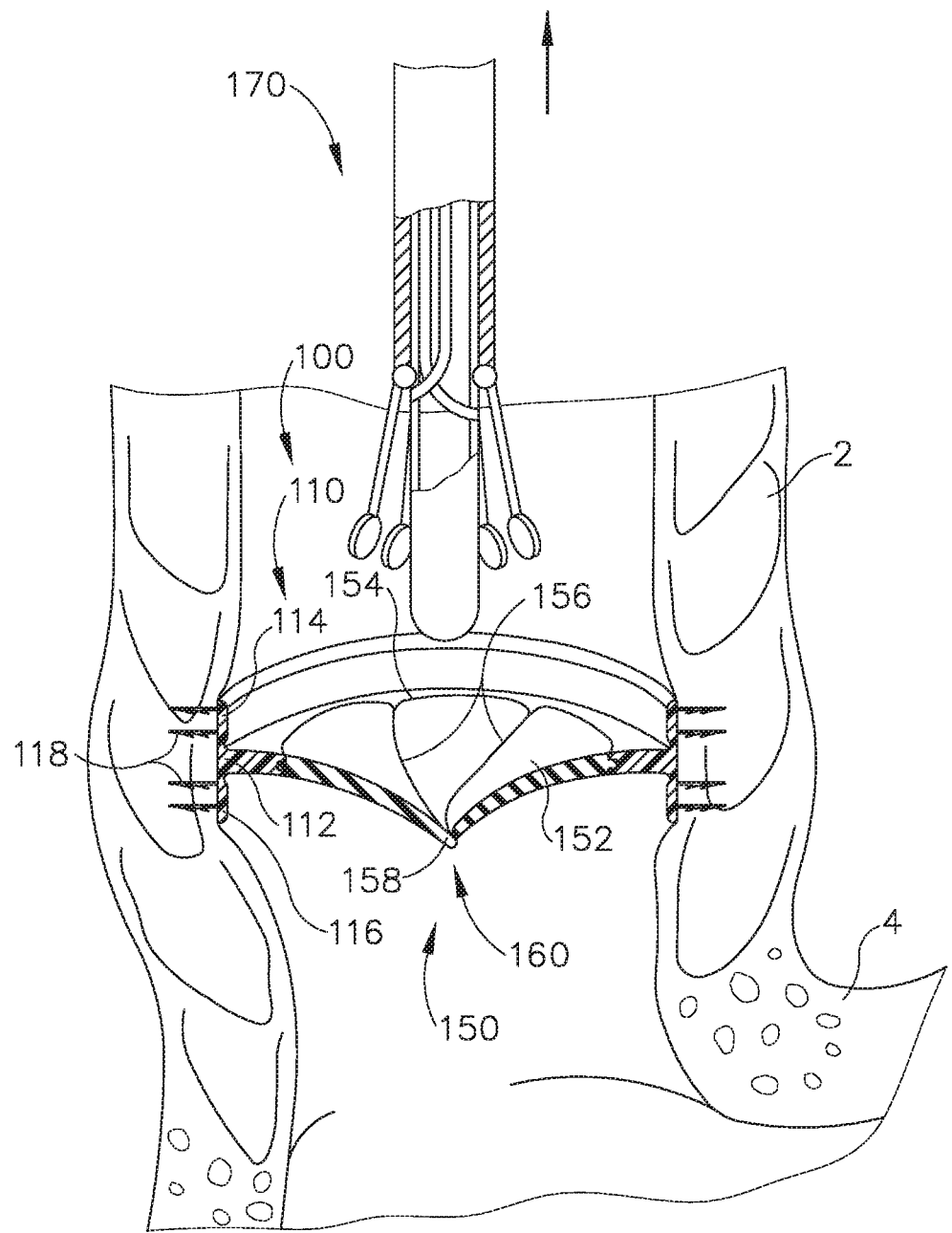
FIG. 7 depicts a cross-sectional isometric view, taken along a coronal plane of the body, of the artificial sphincter implant of FIG. 3 attached to the esophagus of the biological passage of FIG. 1, where the deployment assembly of FIG. 5 is removed from the artificial sphincter implant, with a portion broken away to reveal internal components.
Figure 8A:
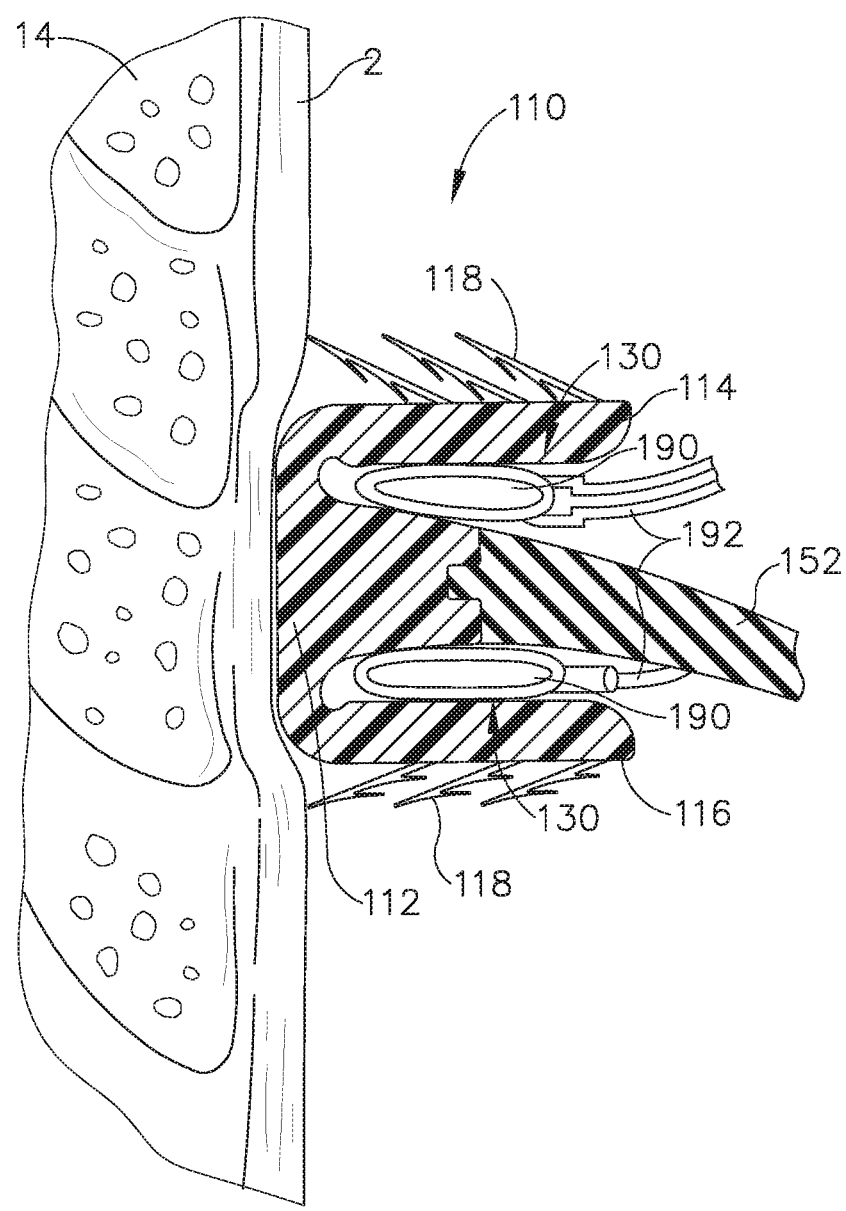
FIG. 8A depicts a cross-sectional side view, taken along a coronal plane of the body, where the deployment assembly of FIG. 5 is inserted into the esophagus of the biological passage of FIG. 1, where the deployment assembly has expanded the artificial sphincter implant of FIG. 3 into the first deployed position.
Figure 8B:
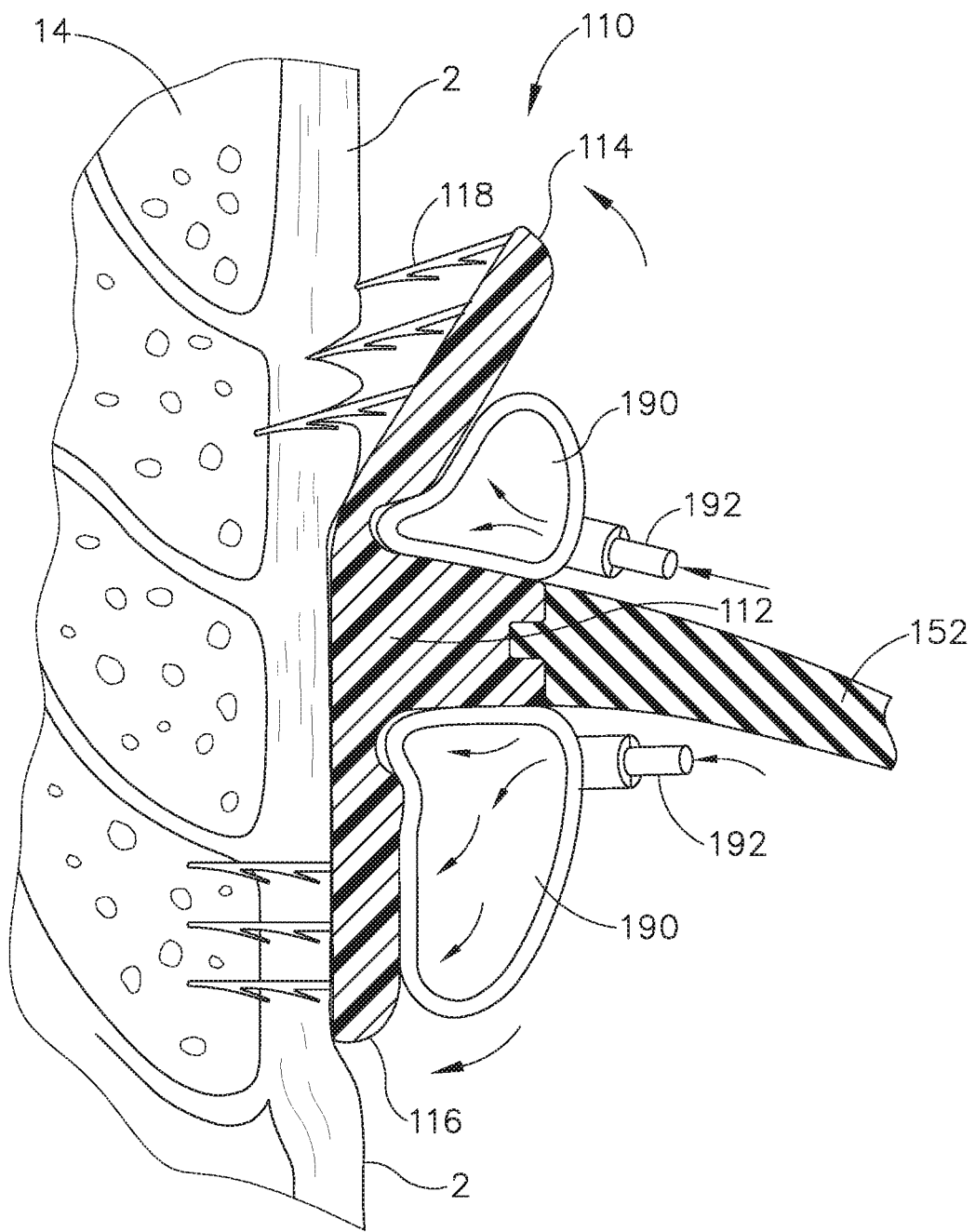
FIG. 8B depicts a cross-sectional side view, taken along a coronal plane of the body, where the deployment assembly of FIG. 5 is inserted into the esophagus of the biological passage of FIG. 1, where the deployment assembly has expanded the artificial sphincter implant of FIG. 3 into a position between the first deployed position and the second deployed position.
Figure 8C:
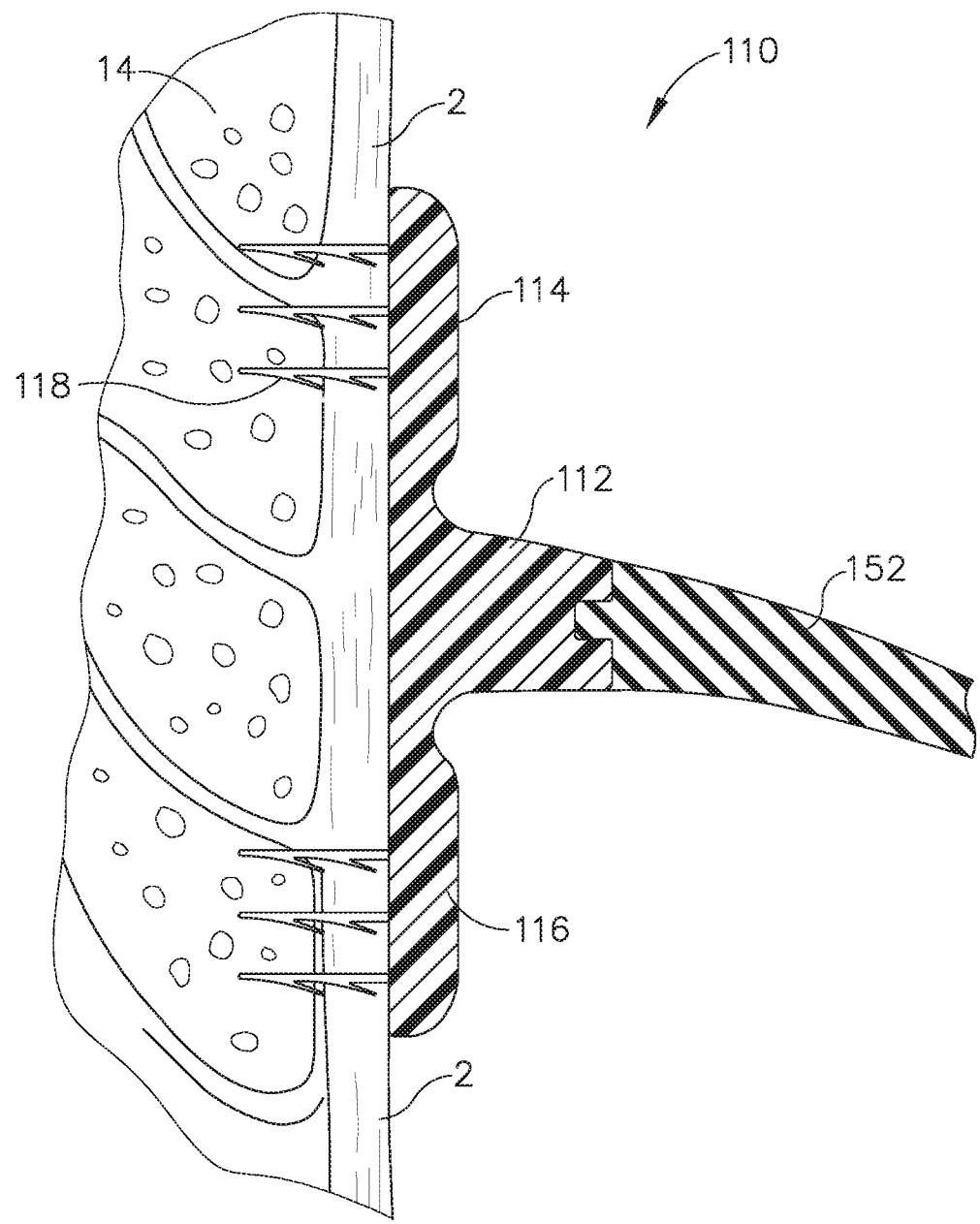
FIG. 8C depicts a cross-sectional side view, taken along a coronal plane of the body, where the deployment assembly of FIG. 5 is inserted into the esophagus of the biological passage of FIG. 1, where the deployment assembly has expanded the artificial sphincter implant of FIG. 3 into the second deployed position.

As best seen between FIGS. 8A-8C, because inflatable members (190) are housed within pockets (130), inflation of inflatable members (190) drives flanges (114, 116) vertically away from valve coupling annular body (112) and toward the interior lining of esophagus (2). Because anchors (118) are attached to flanges (114, 116), anchors (118) are folded radially outwardly, thereby penetrating esophagus (2), and possibly muscularis (14), to secure annular retaining assembly (110) within esophagus (2). In other words, inflation of inflatable members (190) may drive anchors (118) to penetrate an interior surface of esophagus (2). Because inflation of inflatable members (190) drives flanges (114, 116) away from valve coupling annular body (112), temporary pockets (130) are no longer defined when implant (100) transitions into the deployed position (as shown in FIGS. 6C and 8C). Therefore, inflatable members (190) and distal ends (188) of rotatable arms (186) are no longer coupled with implant (100). As best seen in FIG. 7, once inflatable members (190) drive implant (100) into the deployed position, deployment assembly (170) may be removed from esophagus (2) while leaving annular retaining assembly (110) substantially fixed within the interior of esophagus (2).

While implant (100) and deployment assembly (170) of the present example are configured to first radially expand annular retaining assembly (110) and then deploy anchors (118) to engage esophagus (2) in separate stages, this is merely optional. For instance, anchors (118) may be angled on flanges (114, 116) such that anchors (118) may partially engage interior of esophagus (2) when implant (100) is expanded into the second pre-deployed position. Additionally, while anchors (118) are meant to be deployed by being driven radially outwardly in the present example, anchors (118) may also be twisted or rotated about axis (102) to engage esophagus (2).

Alternatively, anchors (118) may be configured to attach to esophagus (2) substantially simultaneously while annular body (112) expands from the first pre-deployed position to the second pre-deployed position. For instance, valve coupling annular body (112) may include a moldable or malleable material such that when annular body (112) expands away from central axis (102) while being deployed (similar to the transition between the first and second pre-deployed position), annular body (112) becomes thinner in the radial direction. Anchors (118) may be entirely housed within annular body (112) before annular body (112) expands in the radial direction. Further, anchors (118) may be attached to an interior portion of annular body (112) such that as annular body (112) expands in the radial direction, anchors (118) start to extend from an exterior surface of annular body (112) in an outward radial direction to engage esophagus (2). Therefore, anchors (118) may be automatically exposed while annular body (112) is expanded. This feature may permit insertion of annular body (112) into a passageway while annular body (112) is in the retracted position and anchor (118) are entirely sheathed. If anchors (18) are in the form of a catch, this feature may permit anchors (118) to pin a portion of the interior of biological passage against annular body (112) when annular body (112) contracts.

As mentioned above, annular retaining assembly (110) may include material that is configured to promote tissue growth after insertion. Additionally, such material may also be absorbable, such that at least a portion of annular retaining assembly (110) breaks down while tissue growth replaces the material to ensure structure integrity of annular retaining assembly (110). FIGS. 9A-9C show an implanted annular retaining assembly (110) including an absorbable material that is configured to promote tissue growth over various periods of time within esophagus (2). Additionally, annular retaining assembly (110) also includes a plurality of inert non-absorbable structures (124) extending within the absorbable material defining valve coupling annular body (112) and flanges (114, 116).

FIG. 9A shows annular retaining assembly (110) just after implantation. At this point, annular retaining assembly (110) is substantially longitudinally fixed relative to esophagus (2) based on the holding strength of anchors (118). Additionally, absorbable material defining anchors (118), valve coupling annular body (112), and flanges (114, 116) are still structurally intact such that absorbable material has yet to break down and tissue in-growth has yet to occur.

After a suitable amount of time after implantation, as shown in FIG. 9B, absorbable material defining valve coupling annular body (112) and flanges (114, 116) starts to break down while tissue in-growth (126) starts to take the place of absorbable material. Inert non-absorbable structures (124) remain intact as they do not break down or promote tissue in-growth (126). Anchors (118) may or may not have begun to break down, but still at least partially help substantially secure annular retaining assembly (110) to esophagus (2). It should be understood at this point, that magnetic sectors (152) are still operable to flex and deform relative to esophagus (2) while portions of magnetic sectors (152) remain substantially spatially fixed relative to esophagus (2).

FIG. 9C show implant (100) after absorbable material defining annular body (120), flanges (114, 116), and anchors (118) has broken down and been structurally replaced by tissue in-growth (126). Therefore, anchors (118) may no longer help spatially fix annular retaining assembly (110) relative to esophagus (2). Non-absorbable structures (124) still remain intact. Magnetic sectors (152) are still operable to flex and deform relative to esophagus (2) while portions of magnetic sectors (152) remain substantially spatially fixed relative to esophagus (2). While tissue in-growth (126) has replaced absorbable material, implant (100) is sufficiently attached to esophagus (2) to remain substantially spatially fixed during operation. However, tissue in-growth (126) has been suitably retarded due to non-absorbable structures (124). While a certain degree of tissue in-growth (126) has been accomplished, it is suitably limited in case an operator wishes to eventually remove implant (100). Therefore, an operator may apply enough force to implant (100), and/or incise tissue in-growth (126), to remove implant from esophagus (2) without damaging esophagus (2), if desired.

IV. Exemplary Internal Artificial Sphincter Implant with Overlapping Magnetic Internal Seals FIGS. 10-12B show an exemplary alternative implant (200) that may be used in place of implant (100) described above. Implant (200) includes an annular retaining assembly (210) and a valve assembly (250). Annular retaining assembly (210) extends circumferentially around a central axis (202), which may be substantially similar to central axis (102) described above. Annular retaining assembly (210) is substantially similar to annular retaining assembly (110) described above. Therefore, annular retaining assembly (210) includes a valve coupling annular body (212), an upper annular flange (214), a lower annular flange (216), a plurality of anchors (218), and notches (220); which are substantially similar to valve coupling annular body (112), upper annular flange (114), lower annular flange (116), anchors (118), and notches (120) described above, respectively.

Figure 12A:
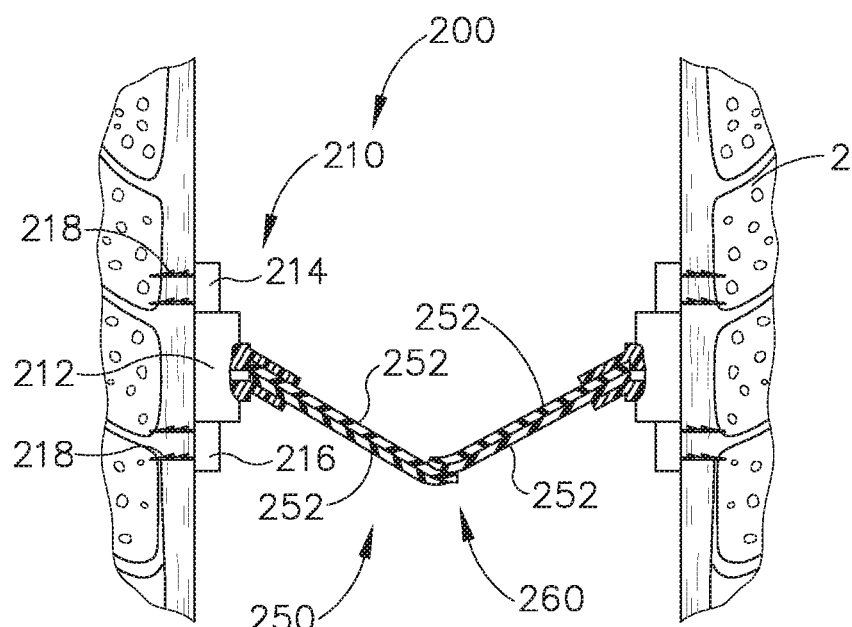
FIG. 12A depicts a cross-sectional side view, taken along a coronal plane of the body, where the artificial sphincter implant of FIG. 10 is operatively attached to the interior portion of the LES of the biological passage of FIG. 1, where the artificial sphincter implant is in an occluded configuration.
Figure 12B:
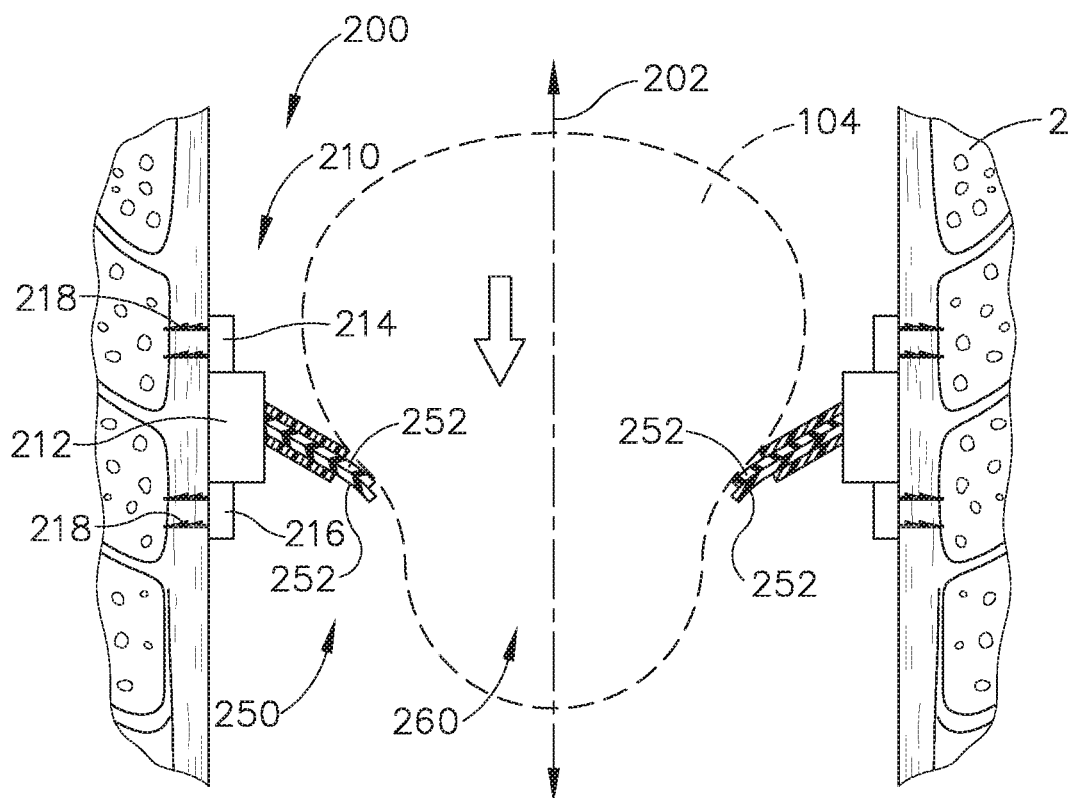
FIG. 12B depicts a cross-sectional isometric view, taken along a coronal plane of the body, where the artificial sphincter implant of FIG. 10 is operatively attached to the interior portion of the LES of the biological passage of FIG. 1, where the artificial sphincter implant is in an opened configuration to accommodate passage of a bolus.

Similar to valve assembly (150) described above, valve assembly (250) includes a plurality of flexible magnetic sectors (252) defining an occludable opening (260) that may transition between an occluded state (FIGS. 10 and 12A) and an opened state (FIG. 12B). Therefore, magnetic sectors (252) utilize a magnetic attraction with adjacent magnetic sectors (252) to bias against each other toward the occluded state. Once a sufficient external force is presented, magnetic sectors (252) may move/flex/bend away from each other toward the opened state. When in the occluded state, magnetic sectors (252) may inhibit solids, liquids, or gasses from passing undesirably through the interior of implant (200) (e.g., from the stomach (4) toward the esophagus (2)). When in the opened state, magnetic sectors (252) may permit solids, liquids, or gasses to pass through the interior of implant (200). Occludable opening (260) may be dimensioned depending on the size of substance passing through occludable opening (260).

Flexible magnetic sectors (252) may be made out the same materials and have similar magnetic pole patterns as magnetic sectors (150) described above. However, flexible magnetic sectors (252) have a different geometry as compared to magnetic sectors (150) described above. Instead of having magnetic sectors (152) with radial perimeter portions (156) directly adjacent to each other with little to no overlap, flexible magnetic sectors (252) overlap with each other such that portions of flexible magnetic sectors (252) are stacked on top of each other to provide a sealing effect.

Each magnetic sector (252) includes a circumferential perimeter portion (254), a top radial perimeter portion (256), a bottom radial perimeter portion (258), and a central arcuate portion (258). Like circumferential perimeter portion (154) described above, circumferential perimeter portion (254) is attached to valve coupling annular body (212) in order to couple each magnetic sector (252) with annular retaining assembly (210). Top radial perimeter portions (256) and bottom radial perimeter portions (258) extend radially toward central axis (202) and terminate into respective arcuate portions (257). Top radial perimeter portion (256) rests on top of adjacent magnetic sectors (252) while bottom radial perimeter portion (258) rests below adjacent magnetic sectors (252) to define an overlapping formation. However, any suitable pattern of layered radial portions may be used as would be apparent to one having ordinary skill in the art in view of the teachings herein. For instance, one magnetic sector (252) may have two radial perimeter portions resting the on the bottom or the top of adjacent magnetic sectors (252).

In the current example, there are four magnetic sectors (252) in a uniform radially extending array that is angularly offset by 90 degrees. However, any suitable number of magnetic sectors (252) may be used and any suitable offset angle(s) may be used as would be apparent to one having ordinary skill in the art in view of the teachings herein. While the radially extending array of magnetic sectors (252) is uniformly offset in the current example, this is merely optional. Additionally, in the current example, circumferential perimeter portion (254) extends circumferentially around central axis (202) approximately 225 degrees. However, circumferential perimeter portion (254) may circumferentially extend around central axis (202) to define any suitable angle as would be apparent to one having ordinary skill in the art in view of the teachings herein.

Figure 10:
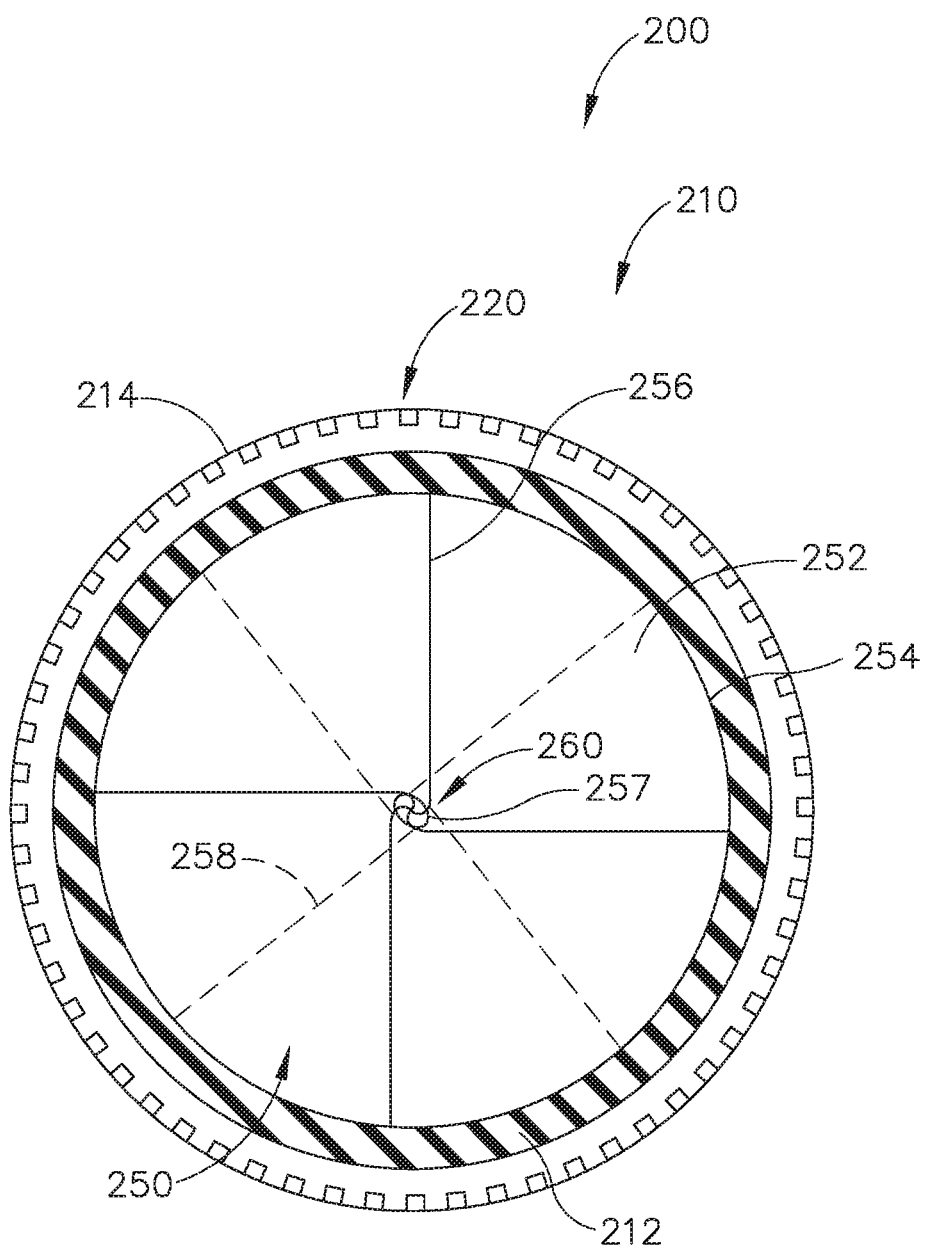
FIG. 10 depicts a cross-sectional top view of an exemplary alternative artificial sphincter implant that may be attached to an interior portion of the LES of the biological passage of FIG. 1.
Figure 11:
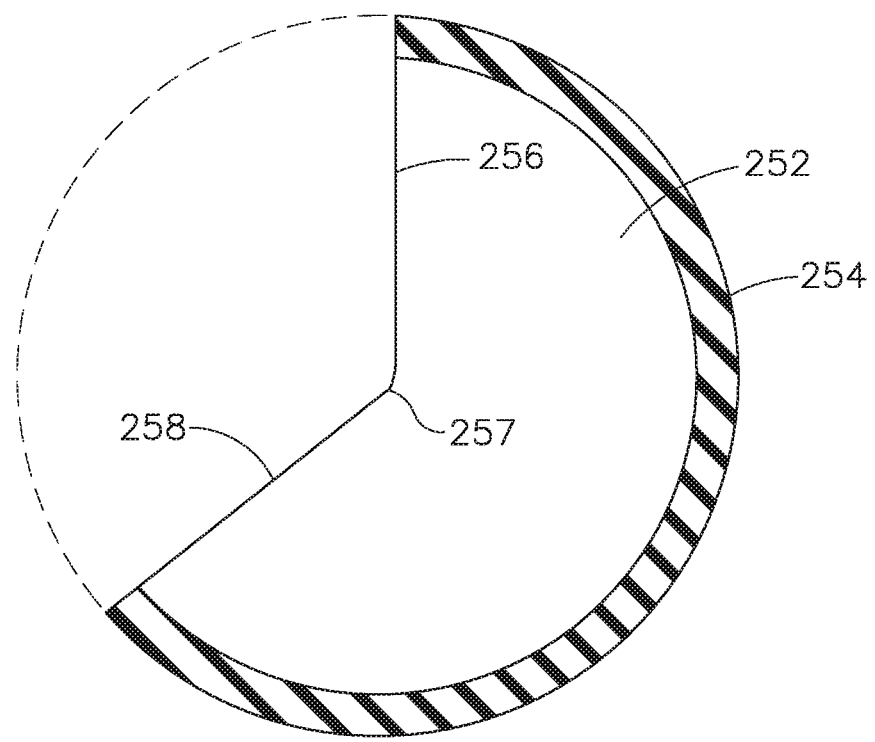
FIG. 11 depicts a cross-sectional top view of an overlapping magnetic petal of the artificial sphincter implant of FIG. 10.

The magnetic poles of magnetic sectors (252) are aligned so that magnetic sectors (252) are magnetically attracted to overlapping portions of adjacent magnetic sectors (252). In particular, the magnetic pole alignment of overlapping portions of magnetic sectors (252) bias toward and against each other such that occludable opening (260) is magnetically biased toward an occluded state (as shown in FIGS. 10 and 12A). Overlapping portions of adjacent magnetic sectors (252) form a seal that inhibits solids, liquids, and gasses from undesirably passing through implant (200). Additionally, magnetic sectors (252) may flexibly deform such that occludable opening (260) transitions from the occluded state to an open state (as shown in FIG. 12B) when a sufficient force overcomes the magnetic attraction between overlapping magnetic sectors (252), thereby pushing and flexing overlapping portions of magnetic sectors (252) away from each other. In the opened state, occludable opening may allow solids, liquids, and gasses to pass through implant (200).

FIGS. 12A-12B show an exemplary use of implant (200) once properly deployed in esophagus (2), where annular retaining assembly (210) remains substantially spatially fixed relative to esophagus (2). It should be understood that implant (200) may be deployed in a substantially similar fashion as implant (100) described above. Therefore, implant (200) is compatible with deployment assembly (170) described above. FIG. 12A shows implant (200) in the occluded state. As described above, the magnetic pole alignment of overlapping portions of magnetic sectors (252) biases magnetic sectors (252) toward and against each other such that occludable opening (260) is naturally in the occluded state. Therefore, magnetic sectors (252) may prevent solids, fluids, and gasses from exiting stomach (4) and entering esophagus (2). In particular, overlapping portions of directly adjacent magnetic sectors (152) may be attracted to each other to promote sufficient contact to provide a sealing effect.

As mentioned above, magnetic sectors (252) may flexibly deform such that occludable opening (260) transitions from the occluded state to an opened state when a sufficient force overcomes the magnetic attraction between adjacent magnetic sectors (252), thereby pushing/flexing/deforming overlapping portions of magnetic sectors (252) away from each other. In the current example, FIG. 12B shows esophagus (2) performing a peristalsis procedure where esophagus (2) is pushing a bolus of food (104) toward stomach (4). The bolus of food (104) provides a sufficient force to overcome the magnetic biasing forces and transition occludable opening (260) into the opened state such that the bolus of food (104) may pass from esophagus (2), through implant (200), and into stomach (4). Therefore, overlapping portions of magnetic sectors (252) space away from each other to allow bolus of food (104) to pass through occludable opening (260) from esophagus (2) into stomach (4).

It should be understood that once bolus of food (104) completely passes through occludable opening (260), a sufficient force overcoming the magnetic biasing forces of magnetic sectors (252) is no longer present. Therefore, the magnetic biasing forces of magnetic sectors (252) urge magnetic sectors (252) back into the occluded state as shown in FIG. 12A.

Magnetic sectors (252) may extend toward central axis in a downward angle. This downwardly angled position of magnetic sectors (252), while in the occluded state, may allow matter to travel in one direction through valve assembly (250) (i.e., from esophagus (2) to stomach (4)) more easily as compared to a second, opposite, direction (i.e., from stomach (4) to esophagus (2)). This may be, at least in part, caused by the geometry of how central arcuate portions (257) interact with each other. Central arcuate portions (257) do not interfere with each other when central arcuate portions (257) flex downwardly, as indicative of matter traveling from esophagus toward stomach (4). However, central arcuate portions (257) do interfere with each other when central arcuate portions (257) flex upwardly, as indicative of matter traveling from stomach (4) toward esophagus (2). This interference may require a larger force to expand occludable opening (260) from the occluded state to the opened state for matter traveling from stomach (4) toward the esophagus (2) as compared to matter traveling from esophagus (2) toward stomach (4).

Figure 13:
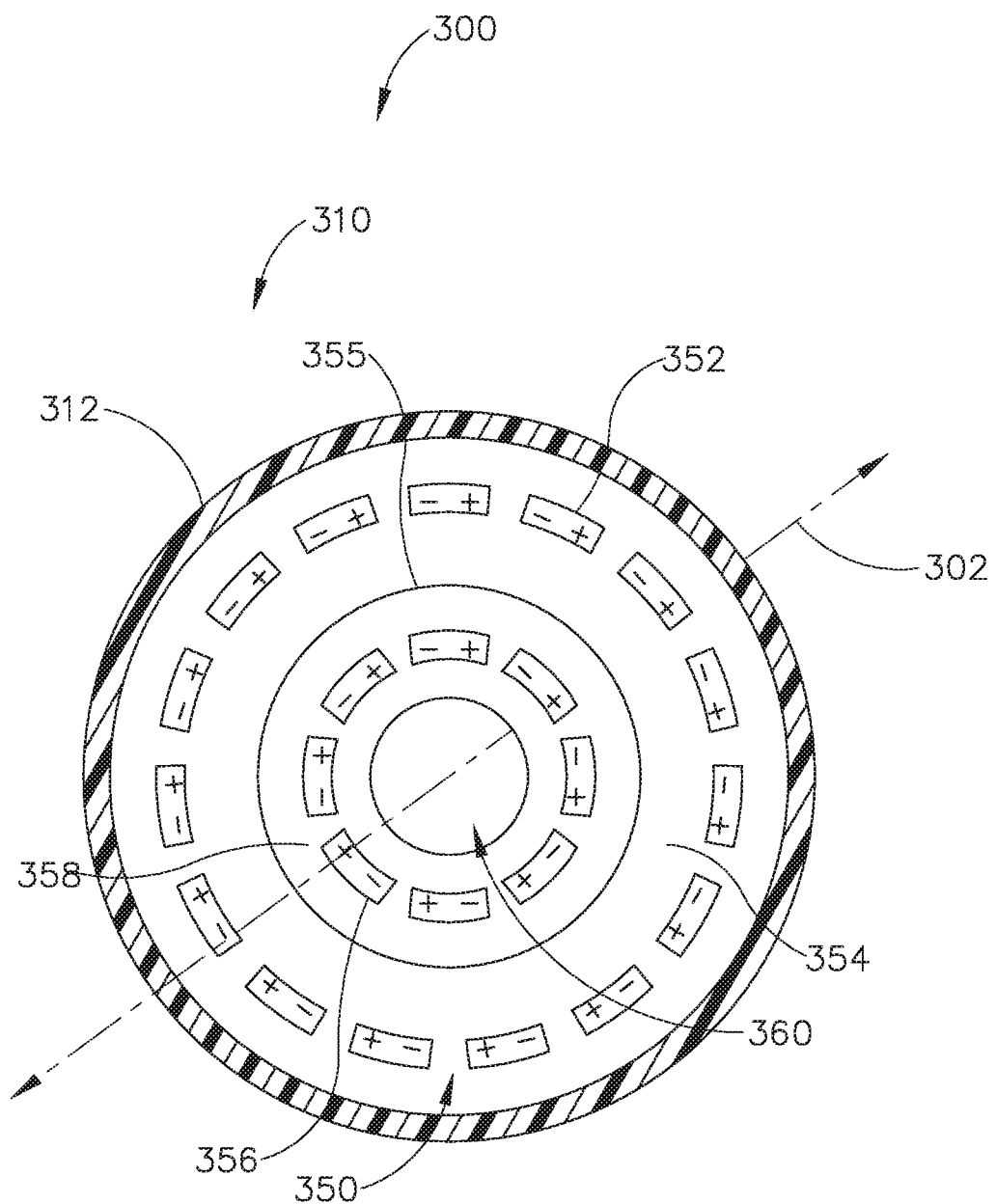
FIG. 13 depicts a cross-sectional top view of an exemplary alternative artificial sphincter implant that may be attached to an interior portion of the LES of the biological passage of FIG. 1.
Figure 14A:
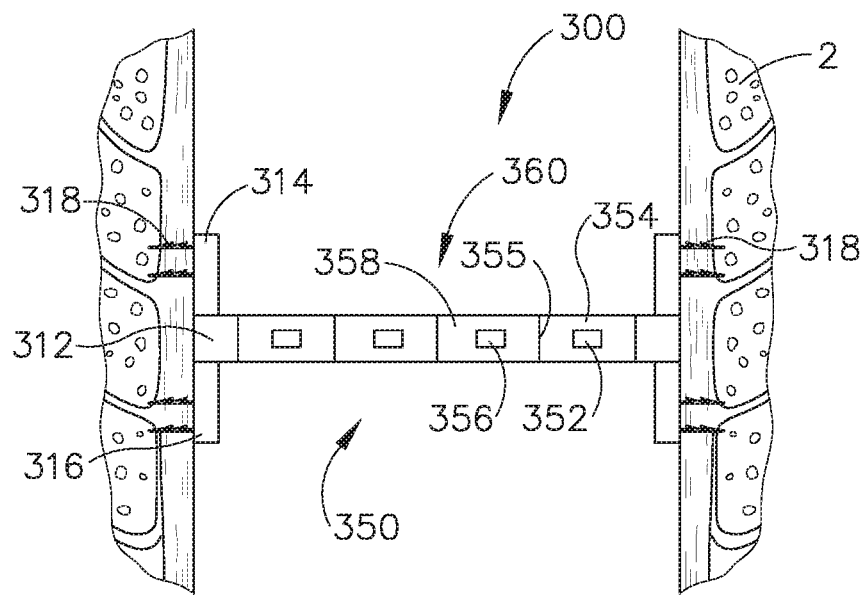
FIG. 14A depicts a cross-sectional side view, taken along a coronal plane of the body, where the artificial sphincter implant of FIG. 13 is operatively attached to the interior portion of the LES of the biological passage of FIG. 1, where the artificial sphincter implant is in an occluded configuration.
Figure 14B:
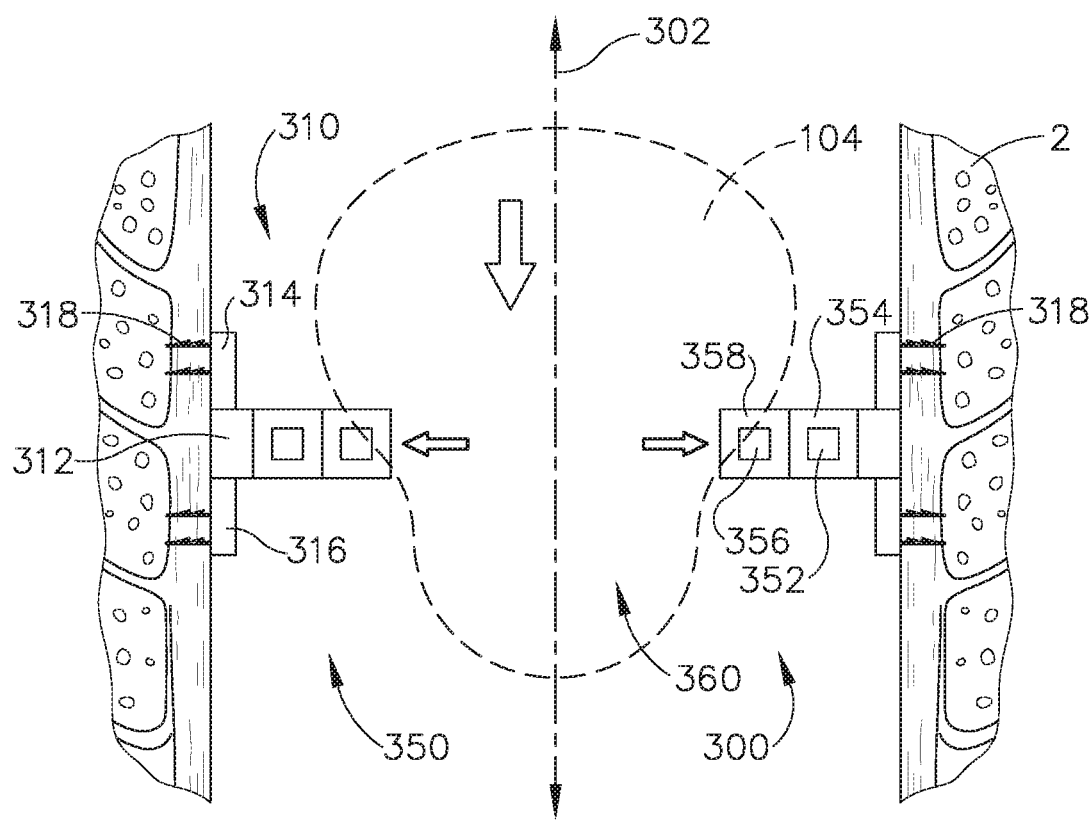
FIG. 14B depicts a cross-sectional isometric view, taken along a coronal plane of the body, where the artificial sphincter implant of FIG. 13 is operatively attached to the interior portion of the LES of FIG. 1, where the artificial sphincter implant is in an opened configuration to accommodate passage of a bolus.

V. Exemplary Internal Artificial Sphincter Implant with Alternative Magnetic Restraints A. Exemplary Internal Artificial Sphincter Implant with Multiple Magnetic Annular Arrays FIGS. 13-14B show another alternative implant (300) that may be used in place of implant (100, 200) described above. Implant (300) includes an annular retaining assembly (310) and a valve assembly (350). Annular retaining assembly (310) extends circumferentially around a central axis (302), which may be substantially similar to central axis (102, 202) described above. Annular retaining assembly (310) is substantially similar to annular retaining assembly (110, 210) described above. Therefore, annular retaining assembly (310) includes a valve coupling annular body (312), an upper annular flange (314), a lower annular flange (316), and a plurality of anchors (318); which are substantially similar to valve coupling annular body (112, 212), upper annular flange (114, 214), lower annular flange (116, 216), and anchors (118, 218) described above, respectively.

Unlike valve assembly (150, 250) described above, valve assembly (350) includes an outer annular array of magnets (352) encased in a first highly flexible silicone sheath (354), and an inner annular array of magnets (356) encased in a second highly flexible silicone sheath (358). Second highly flexible silicone sheath (358) defines an occludable opening (360) that may transition from an occluded state to an opened state. As will be described in greater detail below, magnets (352, 356) are aligned to magnetically bias highly flexible silicone sheath (358) toward the occluded state (as shown in FIG. 14A). Once a sufficient force is presented, first and second highly flexible silicone sheaths (354, 358) may move/flex/bend radially away from central axis (302) such that occludable opening (360) transitions into the opened state (as shown in FIG. 14B). When in the occluded state, valve assembly (350) may inhibit solids, liquids, or gasses from passing undesirably through the interior of implant (300). When in the opened state, valve assembly (350) may permit solids, liquids, or gasses to pass through the interior of implant (300). Occludable opening (360) may be dimensioned depending on the size of substance passing through occludable opening.

Outer annular array of magnets (352) are encased in first highly flexible silicone sheath (354) such that magnets (352) may move toward and away from each other to deform first highly flexible silicone sheath (354). Similarly, inner annular array of magnets (356) are encased in second highly flexible silicone sheath (358) such that magnets (356) may move toward and away from each other in order to deform second highly flexible silicone sheath (358). Outer annular array of magnets (352) and inner annular array of magnets (356) are prevented from overlapping with each other. First and second highly flexible silicone sheaths (354, 358) may have different flexibilities such that one sheath may deform more easily than the other, although this is merely optional. While silicone is used in first and second highly flexible sheaths (354, 358) in the present example, any other suitable elastomer may be used as would be apparent to one having ordinary skill in the art in view of the teachings herein.

First highly flexible silicone sheath (354) and second highly flexible silicone sheath (358) are connected with each other at a sealed juncture (355). Additionally, first highly flexible silicone sheath (354) is attached to an interior surface of valve coupling annular body (312). First highly flexible silicone sheath (354) may be attached to the interior surface of valve coupling annular body (312) such that as first and second highly flexible silicone sheaths (354, 358) expand and contract between the occluded state and the opened state, valve coupling annular body (312) also at least partially expands and contracts in the radial direction. However, this is merely optional. While first highly flexible silicon sheath (354) and second highly flexible silicone sheath (358) connect at a sealed juncture in the current example, a single highly flexible silicone sheath may be used, or more than two highly flexible silicone sheaths may be used.

Outer annular array of magnets (352) are aligned such that opposite poles of adjacent magnets (352) are arranged end to end of one another, thereby promoting a magnetic attraction between adjacent magnets (352). Therefore, outer annular array of magnets (352) are magnetically attracted to each toward each other along a circumferential dimension. Similarly, inner annular array of magnets (356) are aligned such that opposite poles of adjacent magnets (356) are arranged end to end of one another. Therefore, inner annular array of magnets (352) are magnetically attracted to each toward each other along a circumferential dimension. Additionally, the polarity of outer annular array of magnets (352) and inner annular array of magnets (356) are aligned relative to each other such that inner and outer annular array of magnets (356, 352) repel each other in a radial direction. Therefore, outer annular array of magnets (352) may repel inner annular array of magnets (356) radially inwardly toward central axis (302) so second highly flexible silicone sheath (358) is magnetically biased to the occluded state.

In the current example, outer annular array of magnets (352) includes fifteen magnets while inner annular array of magnets (356) includes eight magnets. However, any suitable number of magnets in either array (352, 356) may be used as would be apparent to one having ordinary skill in the art in view of the teachings herein. Additionally, any suitable type of magnet may be used as would be apparent to one having ordinary skill in the art in view of the teachings herein. Further, while the current example has two annular arrays of magnets (352, 356), any suitable number of annular arrays of magnets may be used as would be apparent to one having ordinary skill in the art in view of the teachings herein.

The polarity alignment of magnets (352, 356) magnetically urges second highly flexible silicone sheath (358), as well as occludable opening (360), toward a sealed occluded state (as shown in FIG. 14A). Additionally, when a sufficient force overcomes the magnetic forces between magnets (352, 356), each annular array of magnets (352, 356) may space away from central axis (302) such that first and second highly flexible silicone sheaths (354, 358) may flexibly deform to transition occludable opening (360) from the occluded state to an opened state (as shown in FIG. 14B). In the opened state, occludable opening may allow solids, liquids, and gasses to pass through implant (300).

FIGS. 14A-14B show an exemplary use of implant (300) once properly deployed in esophagus (2). Therefore, annular retaining assembly (310) may remain substantially spatially fixed relative to esophagus (2). It should be understood that implant (300) may be deployed in a substantially similar fashion as implant (100) described above. Therefore, implant (300) is compatible with deployment assembly (170) described above. FIG. 14A shows implant (300) in the occluded state. As described above, the polarity alignment of magnets (352, 356) magnetically urges second highly flexible silicone sheath (358) toward a sealed occluded state. Therefore, valve assembly (350) may prevent the transfer of solids, fluids, and gasses from exiting stomach (4) and entering esophagus (2).

As mentioned above, valve assembly (350) may flexibly deform such that occludable opening (360) transitions from the occluded state to an opened state when a sufficient force overcomes the magnetic forces between annular array of magnets (352, 356), thereby pushing/flexing/deforming highly flexible silicone sheaths (354, 358) away from central axis (302). In the current example, FIG. 14B shows esophagus (2) performing a peristalsis procedure where esophagus (2) is pushing a bolus of food (104) toward stomach (4). The bolus of food (104) provides a sufficient force to overcome the magnetic biasing forces and transition occludable opening (360) into the opened state such that the bolus of food (104) may pass from esophagus (2), through implant (300), and into stomach (4). Therefore, each annular array of magnets (352, 356) spaces away from central axis (302) such that first and second highly flexible silicone sheaths (354, 358) flexibly deform occludable opening (360) into the opened state to allow bolus of food (104) to pass through occludable opening (360) from esophagus (2) into stomach (4).

It should be understood that once bolus of food (104) completely passes through occludable opening (360), a sufficient force overcoming the magnetic biasing forces of magnets (352, 356) is no longer present. Therefore, the magnetic biasing forces of magnets (352, 356) urge first and second highly flexible silicone sheaths (354, 358) back into the occluded state as shown in FIG. 14A.

B. Exemplary Internal Artificial Sphincter Implant with Single Magnetic Annular Array FIGS. 15A-16B show another alternative implant (400) that may be used in place of implant (100, 200, 300) described above. Implant (400) includes an annular retaining assembly (410) and a valve assembly (450). Annular retaining assembly (410) extends circumferentially around a central axis (402), which may be substantially similar to central axis (102, 202, 302) described above. Annular retaining assembly (410) is substantially similar to annular retaining assembly (110, 210, 310) described above. Therefore, annular retaining assembly (410) includes a valve coupling annular body (412), an upper annular flange (414), a lower annular flange (416), and a plurality of anchors (418); which are substantially similar to valve coupling annular body (112, 212, 312), upper annular flange (114, 214, 314), lower annular flange (116, 216, 316), and anchors (118, 218, 318) described above, respectively.

Figure 16A:
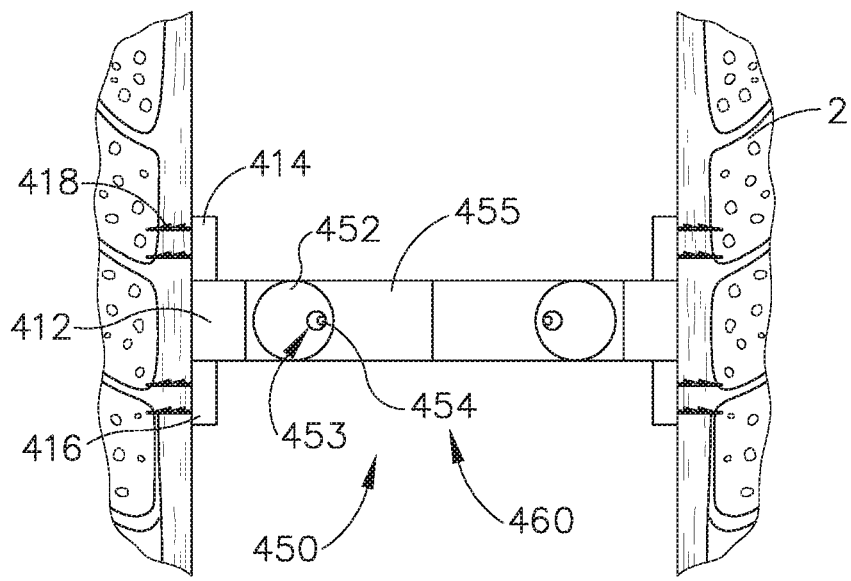
FIG. 16A depicts a cross-sectional side view, taken along a coronal plane of the body, where the artificial sphincter implant of FIG. 15A is operatively attached to the interior portion of the LES of the biological passage of FIG. 1, where the artificial sphincter implant is in an occluded configuration.
Figure 16B:
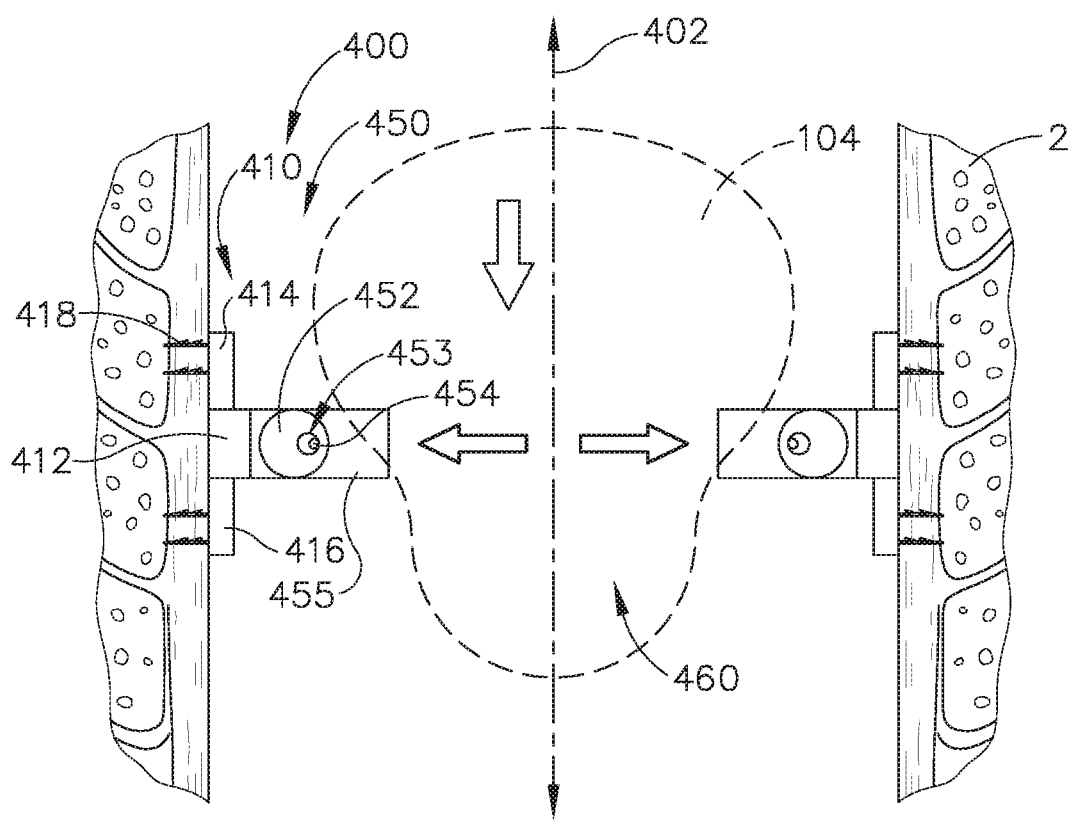
FIG. 16B depicts a cross-sectional isometric view, taken along a coronal plane of the body, where the artificial sphincter implant of FIG. 15A is operatively attached to the interior portion of the LES of FIG. 1, where the artificial sphincter implant is in the opened configuration to accommodate passage of a bolus.

Valve assembly (450) includes an annular array of spherical magnets (452) and spacing members (456) encased in a highly flexible silicone bag (455). Highly flexible silicone bag (455) defines an occludable opening (460) that may transition from an occluded state to an opened state. As will be described in greater detail below, spherical magnets (452) are aligned to magnetically bias highly flexible silicone bag (455) toward the occluded state (as shown in FIG. 16A). Once a sufficient force is presented, highly flexible silicone bag (455) may move/flex/bend radially away from central axis (402) such that occludable opening (460) transitions into the opened state (as shown in FIG. 16B). When in the occluded state, valve assembly (450) may inhibit solids, liquids, or gasses from passing undesirably through the interior of implant (400). When in the opened state, valve assembly (450) may permit solids, liquids, or gasses to pass through the interior of implant (400). Occludable opening (460) may be dimensioned depending on the size of substance passing through occludable opening (460).

Spacing members (456) and spherical magnets (452) are arranged in an alternating annular pattern. Additionally, spacing members (456) and spherical magnets (452) are additionally coupled to each other by a flexible cord (454) extending through pathways (453) defined by both spherical magnets (452) and spacing members (456). Cord (454) may flex to accommodate movement of spherical magnets (452) and spacing members (456) relative to each other.

Figure 15A:
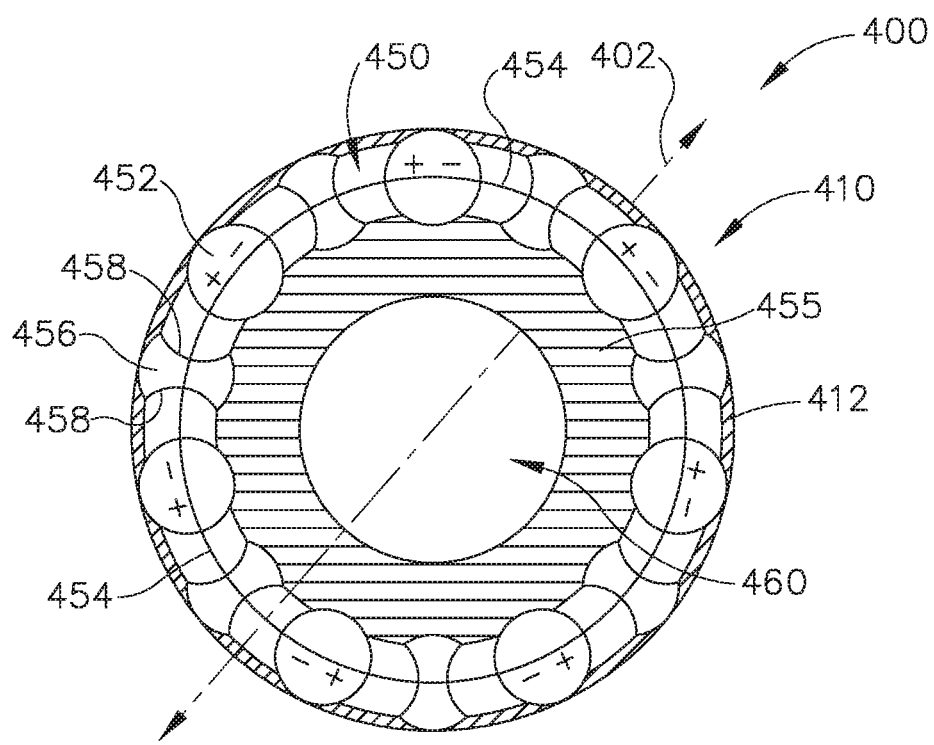
FIG. 15A depicts a cross-sectional top view of an exemplary alternative artificial sphincter implant that may be attached to an interior portion of the LES of the biological passage of FIG. 1, where the artificial sphincter implant is in an opened configuration.
Figure 15B:
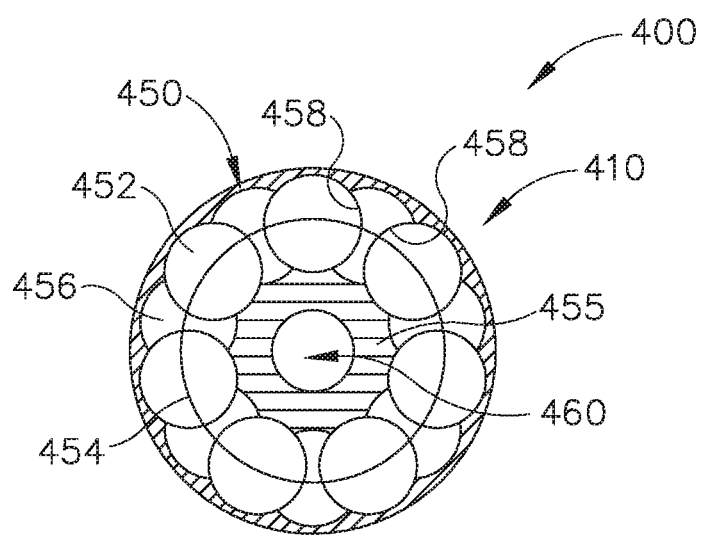
FIG. 15B depicts a cross-sectional top view of an exemplary alternative artificial sphincter implant that may be attached to an interior portion of the LES of the biological passage of FIG. 1, where the artificial sphincter implant is in a partially opened configuration.

As seen between FIGS. 15A-15B, spherical magnets (452) and spacing members (456) may move toward and away each other to deform highly flexible silicone bag (455). Highly flexible silicone bag (455) is connected to an interior surface of valve coupling annular body (412). Highly flexible silicone bag (455) may be attached to the interior surface of valve coupling annular body (412) such that as highly flexible silicone bag (455) expands and contracts between the occluded state and the opened state, valve coupling annular body (412) also at least partially expands and contracts in the radial direction. However, this is merely optional. While silicone is used in highly flexible silicone bag (455) in the current example, any other suitable elastomer may be used as would be apparent to one having ordinary skill in the art in view of the teachings herein.

Spherical magnets (452) are aligned such that opposite poles of adjacent spherical magnets (452) are facing each other in a circumferential pattern, thereby promoting a magnetic attraction between adjacent spherical magnets (452). Therefore, spherical magnets (452) are magnetically attracted to each toward each other along a circumferential dimension. Spacing members (456) each define two complementary arched surfaces (458) facing opposite directions and dimensioned to accommodate at least a portion of adjacent spherical magnets (452) when highly flexible silicone bag (455) is in the occluded state. Therefore, spacing members (456) may control the minimum distance adjacent spherical magnets (452) are relative to each other. Because magnetic force between spherical magnets (452) is at least partially determined by the distance between adjacent spherical magnets (452), spacing members (456) may be dimensioned to control or limit the maximum magnetic attraction force between adjacent spherical magnets (452).

In the current example, seven spherical magnets (452) and seven spacing members (456) are used. However it should be understood that any suitable number of magnets (452) and spacing members (456) may be used as would be apparent to one having ordinary skill in the art in view of the teachings herein. In the current example, spherical magnets (452) include rare earth magnets, however, any other suitable magnet may be used as would be apparent to one having ordinary skill in the art in view of the teachings herein.

The polarity alignment of spherical magnets (452) magnetically urge highly flexible silicone bag (455), as well as occludable opening (460), toward a sealed occluded state (as shown in FIG. 16A). Additionally, when a sufficient force overcomes the magnetic forces between magnets (452), the annular array of spherical magnets (452) and spacing members (456) space away from central axis (402) such that highly flexible silicone bag (455) may flexibly deform to transition occludable opening (460) from the occluded state to the opened state (as shown in FIG. 16B). In the opened state, occludable opening may allow solids, liquids, and gasses to pass through implant (400).

FIGS. 16A-16B show an exemplary use of implant (400) once properly deployed in esophagus (2). Therefore, annular retaining assembly (410) may remain substantially spatially fixed relative to esophagus (2). It should be understood that implant (400) may be deployed in a substantially similar fashion as implant (100) described above. Therefore, implant (400) is compatible with deployment assembly (170) described above. FIG. 16A shows implant (400) in the occluded state. As described above, the polarity alignment of spherical magnets (452) magnetically urges second highly flexible silicone bag (455) toward a sealed occluded state. Therefore, valve assembly (450) may prevent the transfer of solids, fluids, and gasses from exiting stomach (4) and entering esophagus (2).

As mentioned above, valve assembly (450) may flexibly deform such that occludable opening (460) transitions from the occluded state to an opened state when a sufficient force overcomes the magnetic forces between spherical magnets (452), thereby pushing/flexing/deforming highly flexible silicone bag (455) away from central axis (402). In the current example, FIG. 16B shows esophagus (2) performing a peristalsis procedure where esophagus (2) is pushing a bolus of food (104) toward stomach (4). The bolus of food (104) provides a sufficient force to overcome the magnetic biasing forces and transition occludable opening (460) into the opened state such that the bolus of food (104) may pass from esophagus (2), through implant (400), and into stomach (4). Therefore, the annular array of spherical magnets (452) and spacing members (456) space away from central axis (402) such that highly flexible silicone bag (455) flexibly deforms occludable opening (460) into the opened state to allow bolus of food (104) to pass through occludable opening (460) from esophagus (2) into stomach (4).

It should be understood that once bolus of food (104) completely passes through occludable opening (460), a sufficient force overcoming the magnetic biasing forces of spherical magnets (452) is no longer present. Therefore, the magnetic biasing forces of magnets (452) urge the annular array of spherical magnets (452) and spacing members (456) toward each other, and therefore highly flexible silicone bag (455) back into the occluded state as shown in FIG. 16A.

Figure 17:
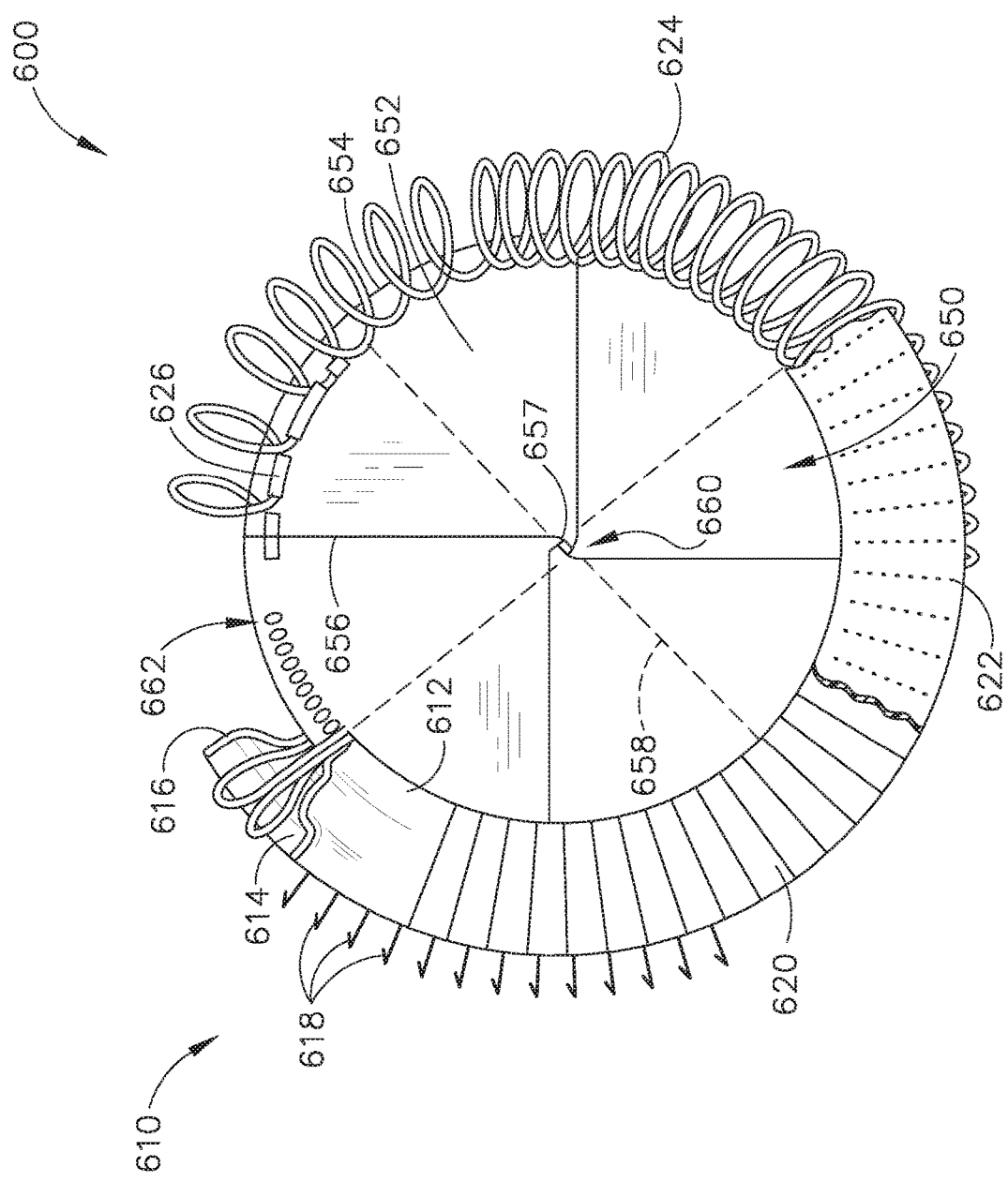
FIG. 17 depicts a top plan view of an exemplary alternative artificial sphincter implant that may be attached to an interior portion of the LES of the biological passage of FIG. 1.

VI. Exemplary Alternative Artificial Implant with Alternative Annular Retaining Assemblies FIG. 17 shows an exemplary alternative artificial implant (600) that may be used in place of implant (200) described above. Therefore, artificial implant (600) may function substantially similar to implant (200) described above, with differences elaborated below. Implant (600) may be inserted and deployed within esophagus (2) via deployment assembly (170) in accordance with the principles described above. Implant (600) includes an annular retaining assembly (610) and a valve assembly (650) defining an occludable opening (660). Valve assembly (650) is substantially similar to valve assembly (250) described above, with difference elaborated below. Therefore, valve assembly (650) includes a plurality of overlapping magnetic sectors (652), each including a circumferential perimeter portion (654), a top radial perimeter portion (656), a bottom radial perimeter portion (658), and a central arcuate portion (657); which are substantially similar to overlapping magnetic sectors (252), each including a circumferential perimeter portion (254), a top radial perimeter portion (256), a bottom radial perimeter portion (258), and a central arcuate portion (257) described above, respectively. Therefore, magnetic sectors (652) are configured to transition from an occluded state to an opened state when properly deployed within the interior of an esophagus (2).

Additionally, each magnetic sector (652) defines a circumferential array of openings (662). As will be described in greater detail below, circumferential array of openings (662) are configured to couple each magnetic sector (652) with an inert portion of annular retaining assembly (610).

Similar to annular retaining assembly (110) described above, annular retaining assembly (610) includes a valve coupling annular body (612), an upper annular flange (614), a lower annular flange (616), and a plurality of anchors (618) which may substantially similar to valve coupling annular body (112), an upper annular flange (114), lower annular flange (616), and plurality of anchors (118) described above, respectively, with differences elaborated below. As mentioned above, annular retaining assembly (110) may include a combination of materials including inert materials as well as absorbable materials that promote tissue growth. As also mentioned above, it may be desirable to promote a sufficient amount of tissue growth after deploying of implant (600) to help spatially fix implant (600) during operation, while also suitably retarding such tissue growth such that an operator may selectively remove implant (600) from esophagus (2) if desired. Annular retaining assembly (610) includes a sufficient combination of inert materials and absorbable materials promoting tissue growth to achieve both functions.

In the present example, valve coupling annular body (612) and flanges (614, 616) are defined by an outer weave (620) filled with vertical column-like threads (622). Outer weave (620) may cover exterior portions of annular body (612) and flanges (614, 616) while vertical column-like threads (622) may fill an interior portion of outer weave (620) to fill out annular body (612) and flanges (614, 616). Therefore, outer weave (620) has an exterior surface facing away from column-like threads (622) and an interior surface that is adjacent to column-like threads (622). Outer weave (620) may be made out of an absorbable material such that over a period of time after deployed within esophagus (2), outer wave (620) may dissolve. Vertical column-like threads (622) may be made out of a material configured to promote a suitable amount of tissue growth such that implant (600) may remain stationary during operation, but also such that implant (600) may be removed from esophagus (2) when desired without causing substantial damage. Of course, outer weave (620) and vertical column-like threads (622) may be both made out of absorbable material configured to promote tissue growth such that after a suitable time deployed within esophagus (2), tissue begins to grow around and/or replace outer weave (620) and vertical column-like threads (622). Any other suitable combination of materials for outer weave (620) and vertical column-like threads (622) may be used as would be apparent to one having ordinary skill in the art in view of the teachings herein. Outer weave (620) and vertical column-like threads (622) may form a fibrous absorbable lattice that may include both absorbable polymers and non-absorbable polymers such as nylon and polypropylene.

The materials for valve coupling annular body (612) and flanges (614, 616) can include bioabsorbable and biocompatible polymers, including homopolymers and copolymers. Non-limiting examples of homopolymers and copolymers include p-dioxanone (PDO or PDS), polyglycolic acid (PGA), poly(lactic-co-glycolic acid) (PLGA), polycaprolactone (PCL), trimethylene carbonate (TMC), and polylactic acid (PLA), poly(glycolic acid-co-lactic acid) (PLA/PGA) (e.g., PLA/PGA materials used in Vicryl, Vicryl Rapide, PolySorb, and Biofix), polyurethanes (such as Elastane, Biospan, Tecoflex, Bionate, and Pellethane fibers), polyorthoesters, polyanhydrides (e.g., Gliadel and Biodel polymers), polyoxaesters, polyesteramides, and tyrosine-based polyesteramides. The copolymers can also include polylactic acid-co-polycaprolactone) (PLA/PCL), poly (L-lactic acid-co-poly caprolactone) (PLLA/PCL), poly(glycolic acid-co-trimethylene carbonate) (PGA/TMC) (e.g., Maxon), Poly(glycolic acid-co-caprolactone) (PCL/PGA) (e.g., Monocryl and Capgly), PDS/PGA/TMC (e.g., Biosyn), PDS/PLA, PGA/PCL/TMC/PLA (e.g., Caprosyn), and LPLA/DLPLA (e.g., Optima). The polymers may also have medicants, such examples may also be further constructed and operable in accordance with at least some of the teachings of U.S. Pub. No. 2017/0055986, entitled "Medicant Eluting Adjuncts and Methods of Using Medicant Eluting Adjuncts," published Mar. 2, 2017, issued as U.S. Pat. No. 10,569,071 on Feb. 25, 2020, the disclosure of which is incorporated by reference herein.

Circumferential perimeter portions (654) may extend into portions of outer weave (620) and vertical column-like threads (622) such that outer weave (620) and vertical column-like threads (622) are attached to magnetic sectors (652) before outer weave (620) and vertical column-like threads (622) are absorbed. Outer weave (620) and vertical column-like threads (622) may be resiliently compressible such that outer weave (620) and column-like threads (622) may deform in response to an external force and then return to a natural shape.

Additionally, annular retaining assembly (610) includes a coiled suture (624) that is initially housed within valve coupling annular body (612). Coiled suture (624) may be made out of an inert material. Coiled suture (624) may couple with each magnetic sector (652) via coupling means (626) or through circumferential array of opening (662).

Coiled suture (624) is configured to hold together overlapping magnetic sectors (652) after valve coupling annular flanges (612) and flanges (614, 616) are absorbed. Coiled suture (624) may sufficiently retard tissue growth around overlapping magnetic sectors (652) such that when an operator desires to remove implant (600) from esophagus (2), removal may limit tissue damage around adjacent portions of esophagus (2). Additionally, coiled suture (624) may keep magnetic sectors (652) suitably connected to each other. Therefore, coiled suture (624) may spatially fix magnetic sectors (652) relative to each other after outer weave (620) and vertical column-like threads (622) are absorbed. Additionally, coiled suture (624) may allow magnetic sectors (652) to be removed unitarily from esophagus (2) after outer weave (620) and vertical column-like threads (622) are absorbed.

Valve coupling annular body (612), upper annular flange (614), lower annular flange (616), anchors (618), coiled suture (624), outer weave (620), vertical column-like threads (622), or any suitable combinations/portions therefore may include a coating or therapeutic substance. A coating may include an inert material. The therapeutic substances may include an agent configured to heal tissue from a disease, defect, infection, inflammation, trauma, or any combination thereof. The therapeutic substances may include an agent configured to physically protect tissue from acidic compounds, such as agents that act to neutralize an acidic compound. The therapeutic substances may include a drug, a steroid, an antibiotic, or any other suitable substance that would be apparent to one having ordinary skill in the art in view of the teachings herein. Non-limiting examples of therapeutic substances may include antimicrobial agents, antifungal agents, anti-inflammatory agents, and growth factors. Non-limiting examples of antimicrobial agents include Ionic Silver, Triclosan, Tetracyclines, Doxycycline, Minocycline, Demeclocycline, Tetracycline, Oxytetracycline, Gentamicin, Neomycin, Non-limiting examples of antifungal and antimicrobial agents include Triclosan, Triazole, Thiazole, LAE, Sodium Stearate, Non-limiting examples of anti-inflammatory agents include non-steroidal anti-inflammatory agents (e.g., Salicylates, Aspirin, Diflunisal, Propionic Acid Derivatives, Ibuprofen, Naproxen, Fenoprofen, and Loxoprofen), acetic acid derivatives (e.g., Tolmetin, Sulindac, and Diclofenac), enolic acid derivatives (e.g., Piroxicam, Meloxicam, Droxicam, and Lornoxicam), anthranilic acid derivatives (e.g., Mefenamic Acid, Meclofenamic Acid, and Flufenamic Acid), selective COX-2 inhibitors (e.g., Celecoxib (Celebrex), Parecoxib, Rofecoxib (Vioxx), Sulfonanilides, Nimesulide, and Clonixin), immune selective anti-inflammatory derivatives, corticosteroids (e.g., Dexamethasone), and iNOS inhibitors, Non-limiting examples of growth factors include those that are cell signaling molecules that stimulate cell growth, healing, remodeling, proliferation, and differentiation. Exemplary growth factors can be short-ranged (paracrine), long ranged (endocrine), or self-stimulating (autocrine). Further examples of the growth factors include growth hormones (e.g., a recombinant growth factor, Nutropin, Humatrope, Genotropin, Norditropin, Saizen, Omnitrope, and a biosynthetic growth factor), Epidermal Growth Factor (EGF) (e.g., inhibitors, Gefitinib, Erlotinib, Afatinib, and Cetuximab), heparin-binding EGF like growth factors (e.g., Epiregulin, Betacellulin, Amphiregulin, and Epigen), Transforming Growth Factor alpha (TGF-a), Neuroregulin 1-4, Fibroblast Growth Factors (FGFs) (e.g., FGF1-2, FGF2, FGF11-14, FGF18, FGF15/19, FGF21, FGF23, FGF7 or Keratinocyte Growth Factor (KGF), FGFIO or KGF2, and Phenytoin), Insuline-like Growth Factors (IGFs) (e.g., IGF-1, IGF-2, and Platelet Derived Growth Factor (PDGF)), Vascular Endothelial Growth Factors (VEGFs) (e.g., inhibitors, Bevacizumab, Ranibizumab, VEGF-A, VEGF-B, VEGF-C, VEGF-D and Becaplermin). The therapeutic substances may also include other medicants, such examples may also be further constructed and operable in accordance with at least some of the teachings of U.S. Pub. No. 2017/0055986, entitled "Medicant Eluting Adjuncts and Methods of Using Medicant Eluting Adjuncts," published Mar. 2, 2017, issued as U.S. Pat. No. 10,569,071 on Feb. 25, 2020, the disclosure of which is incorporated by reference herein.

Additionally, therapeutic substances may be embedded in a hollow area, such as a porous portion, of valve coupling annular body (612), upper annular flange (614), lower annular flange (616), anchors (618), coiled suture (624), outer weave (620), or vertical column-like threads (622). Therapeutic substances may be configured to elute from a portion of the artificial sphincter into the tissue of the biological passageway.

Figure 18:
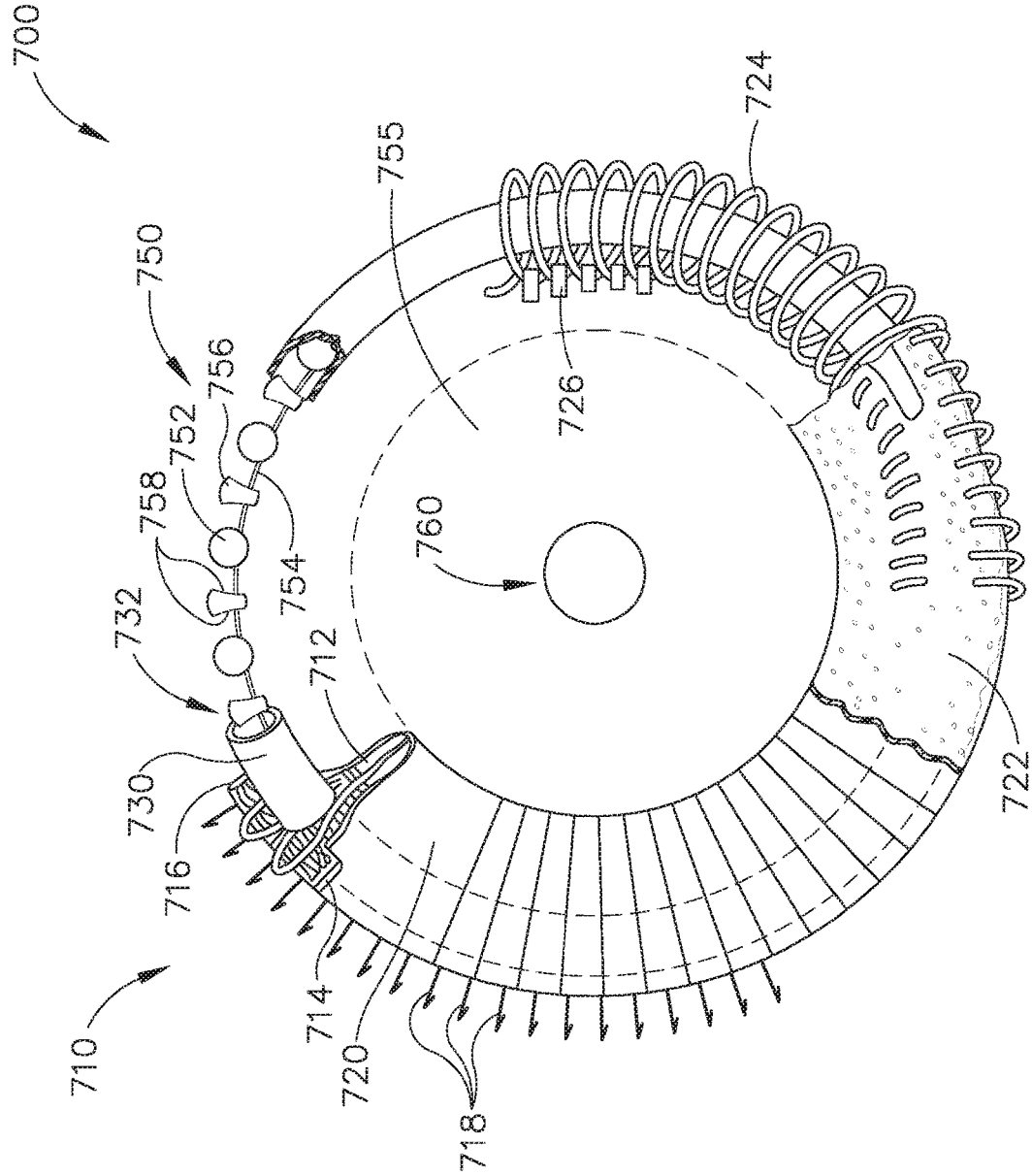
FIG. 18 depicts a top plan view of an exemplary alternative artificial sphincter implant that may be attached to an interior portion of the LES of the biological passage of FIG. 1.

FIG. 18 shows an exemplary alternative artificial implant (700) that may be used in place of implant (400) described above. Therefore, implant (700) may function substantially similar to implant (400) described above, with differences elaborated below. Implant (700) may be inserted and deployed within esophagus (2) via deployment assembly (170) in accordance with the principles described above. Implant (700) includes an annular retaining assembly (710) and a valve assembly (750) defining an occludable opening (760). Valve assembly includes an annular array of spherical magnets (752) and spacing members (756) coupled together by a flexible cord (754), and a highly flexible silicone bag (755) defining occludable opening (760). Spherical magnets (752), spacing members (756), flexible cord (754) and highly flexible silicon bag (755) are substantially similar to spherical magnets (452), spacing members (456), flexible cord (454) and highly flexible silicone bag (455) described above, respectively, with differenced described below.

While spherical magnets (452) and spacing members (456) are housed within highly flexible silicone bag (455), spherical magnets (752) and spacing members (756) are housed within a magnetic assembly housing (732) defined by a flexible internal annular sleeve (730) located within annular retaining assembly (710). Annular retaining assembly (710) may be include a non-absorbable material. Additionally, highly flexible silicone bag (755) is also coupled to annular retaining assembly (710). Therefore, annular retaining assembly (710) acts as an intermediary between spherical magnets (752) and highly flexible silicone bag (755). In other words, when spherical magnets (752) and spacing members (756) move relative to each other radially, both annular retaining assembly (710) and highly flexible silicone bag (755) also move radially to transition occludable opening (760) between the occluded state and the opened state.

Similar to annular retaining assembly (410) described above, annular retaining assembly (610) includes a valve coupling annular body (612), an upper annular flange (614), a lower annular flange (616), and a plurality of anchors (618), which may substantially similar to valve coupling annular body (412), upper annular flange (414), lower annular flange (416), and plurality of anchors (418) described above, respectively, with differences elaborated below. As mentioned above, annular retaining assembly (110) may include a combination of materials including inert materials as well as absorbable materials that promote tissue growth. As also mentioned above, it may be desirable to promote a sufficient amount of tissue growth after deploying of implant (700) to help spatially fix implant (700) during operation, while also suitably retarding such tissue growth such that an operator may selectively remove implant (700) from esophagus (2) if desired. Annular retaining assembly (710) includes a sufficient combination of inert materials and absorbable materials promoting tissue growth to achieve both functions.

In particular, valve coupling annular body (712) and flanges (714, 716) are defined by an outer weave (720) filled with vertical column-like threads (722). Internal annular sleeve (730) may be made out of an inert material and extend within valve coupling annular body (712). Outer weave (720) may cover exterior portions of annular body (712) and flanges (714, 716) while vertical column-like threads (722) may fill an interior portion of outer weave (720) to fill out annular body (712) and flanges (714, 716). Therefore, outer weave (720) has an exterior surface facing away from column-like threads (722) and an interior surface that is adjacent to column-like threads (722). Outer weave (720) may be made out of an absorbable material such that over a period of time after deployed within esophagus (2), outer wave (720) may dissolve.

Vertical column-like threads (722) may be made out of a material that is configured to promote a suitable amount of tissue growth such that implant (700) may remain stationary during operation, but also such that implant (700) may be removed from esophagus (2) when desired without causing substantial damage. Of course, outer weave (720) and vertical column-like threads (722) may both be made of absorbable material that is configured to promote tissue growth such that after a suitable time deployed within esophagus (2), tissue begins to grow around and/or replace outer weave (720) and vertical column-like threads (722). Or, any other suitable combination of materials for outer weave (720) and vertical column-like threads (722) may be used as would be apparent to one having ordinary skill in the art in view of the teachings herein. Outer weave (720) and vertical column-like threads (722) may form a fibrous absorbable lattice that may include both absorbable polymers and non-absorbable polymers such as nylon and polypropylene.

The materials for valve coupling annular body (712) and flanges (714, 716) can include bioabsorbable and biocompatible polymers, including homopolymers and copolymers. Non-limiting examples of homopolymers and copolymers include p-dioxanone (PDO or PDS), polyglycolic acid (PGA), poly(lactic-co-glycolic acid) (PLGA), polycaprolactone (PCL), trimethylene carbonate (TMC), and polylactic acid (PLA), poly(glycolic acid-co-lactic acid) (PLA/PGA) (e.g., PLA/PGA materials used in Vicryl, Vicryl Rapide, PolySorb, and Biofix), polyurethanes (such as Elastane, Biospan, Tecoflex, Bionate, and Pellethane fibers), polyorthoesters, polyanhydrides (e.g., Gliadel and Biodel polymers), polyoxaesters, polyesteramides, and tyrosine-based polyesteramides. The copolymers can also include polylactic acid-co-polycaprolactone) (PLA/PCL), poly (L-lactic acid-co-polycaprolactone) (PLLA/PCL), poly(glycolic acid-co-trimethylene carbonate) (PGA/TMC) (e.g., Maxon), Poly (glycolic acid-co-caprolactone) (PCL/PGA) (e.g., Monocryl and Capgly), PDS/PGA/TMC (e.g., Biosyn), PDS/PLA, PGA/PCL/TMC/PLA (e.g., Caprosyn), and LPLA/DLPLA (e.g., Optima). The polymers may also have medicants, such examples may also be further constructed and operable in accordance with at least some of the teachings of U.S. Pub. No. 2017/0055986, entitled "Medicant Eluting Adjuncts and Methods of Using Medicant Eluting Adjuncts," published Mar. 2, 2017, issued as U.S. Pat. No. 10,569,071 on Feb. 25, 2020, the disclosure of which is incorporated by reference herein.

An outer edge of highly flexible silicone bag (755) may extend into portions of outer weave (720) and vertical column-like threads (722) such that outer weave (720) and vertical column-like threads (722) are attached to highly flexible silicone bag (755) before outer weave (720) and vertical column-like threads (722) are absorbed. As shown in FIGS. 19A-19B, outer weave (720) and vertical column-like threads (722) may be resiliently compressible such that outer weave (720) and column-like threads (722) may deform in response to an external force and then return to a natural shape. FIG. 19A shows the natural shape of column-like threads (722) while FIG. 19B shows column-like threads (722) in a compressed state.

Additionally, annular retaining assembly (710) includes a coiled suture (724) that is initially housed within valve coupling annular body (712). Coiled suture (724) may be made out of an inert material. Coiled suture (724) surrounds internal annular sleeve (730) such that coiled suture (724) may expand and contract with internal annular sleeve (730) in accordance with the principles described above. Coiled suture (724) may also couple with highly flexible silicone base (755) via coupling means (726). Coiled suture (624) is configured to couple internal annular sleeve (730) and highly flexible silicone bag (755) after valve coupling annular flanges (712) and flanges (714, 716) are absorbed. Coiled suture (724) may sufficiently retard tissue growth around internal annular sleeve (730) and highly flexible silicone bag (755) such that when an operator desires to remove implant (700) from esophagus (2), removal may limit tissue damage around adjacent portions of esophagus (2). Therefore, coiled suture (724) may spatially fix internal annular sleeve (730) and highly flexible silicone bag (755) relative to each other after outer weave (720) and vertical column-like threads (722) are absorbed. Additionally, coiled suture (724) may allow for annular sleeve (730) and highly flexible silicone bag (755) to be removed unitarily from esophagus (2) after outer weave (720) and vertical column-like threads (722) are absorbed.

Figure 20B:
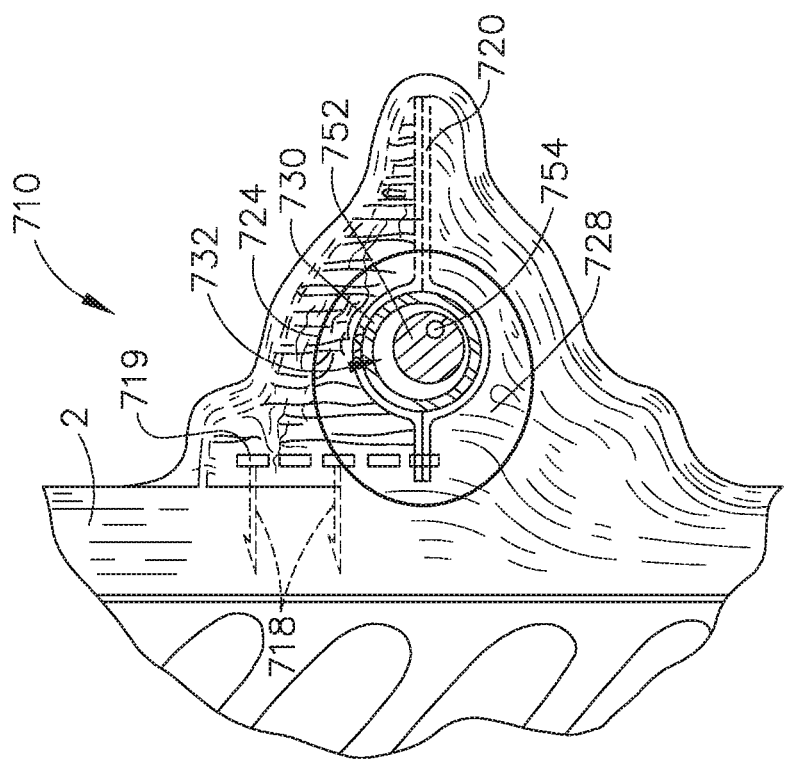
FIG. 20B depicts a cross-sectional side view, taken along a coronal plane of the body, after a sufficient period of time after the artificial sphincter implant of FIG. 18 has been operatively attached to the interior portion of the LES of the biological passage of FIG. 1 such that there is full tissue ingrowth around portions of the artificial sphincter implant.
Figure 20A:
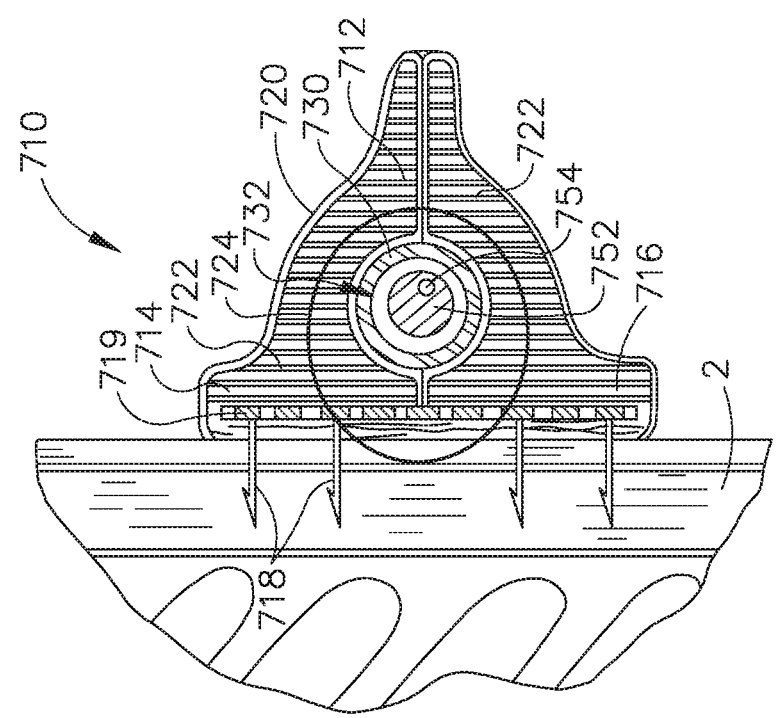
FIG. 20A depicts a cross-sectional side view, taken along a coronal plane of the body, immediately after the artificial sphincter implant of FIG. 18 has been operatively attached to the interior portion of the LES of the biological passage of FIG. 1.

FIGS. 20A-20B show an implanted annular retaining assembly (710) over various periods of time within esophagus (2). Additionally, anchors (718) extend from scaffold members (719) that act to fix a portion of anchors (718) within vertical column-like threads (722). FIG. 20A shows annular retaining assembly (710) just after implantation. At this point, annular retaining assembly (710) is substantially spatially fixed relative to esophagus (2) based on the holding strength of anchors (718). Additionally, absorbable material defining anchors (118), outer wave (720), and vertical column-like threads (722) are still structurally intact such that absorbable material has yet to break down and tissue growth has yet to occur.

After a suitable amount of time after implantation, as shown in FIG. 20B, absorbable material defining anchors (718), outer wave (720), and vertical column-like threads (722) has broken down and been structurally replaced by tissue growth. Therefore, anchors (718) may no longer help spatially fix annular retaining assembly (710) relative to esophagus (2). Non-absorbable structures such as internal annular sleeve (730) and coiled suture (734) still remain intact. Spherical magnets (752) and spacing members (756) are still operable to space toward and away from each other to occlude esophagus (2). While tissue growth has replaced absorbable material of anchors (718), outer weave (720), and vertical column-like threads (722); implant (700) is sufficiently attached to esophagus (2) to remain substantially spatially fixed during operation. However, tissue growth has been suitably retarded due to non-absorbable structures such as coiled suture (724) and internal annular sleeve (730). While a certain degree of tissue growth has been accomplished, it is suitably limited in case an operator wishes to remove implant (700). Therefore, an operator may apply enough force to implant (700), and/or incise tissue, to remove implant from esophagus (2) without damaging esophagus (2), if desired.

Valve coupling annular body (772), upper annular flange (714), lower annular flange (716), anchors (718), coiled suture (724), outer weave (720), vertical column-like threads (722), internal annular sleeve (730), or any suitable combinations/portions therefore may include a coating or therapeutic substance. A coating may include an inert material. The therapeutic substances may include an agent configured to heal tissue from a disease, defect, infection, inflammation, trauma, or any combination thereof. The therapeutic substances may include an agent configured to physically protect tissue from acidic compounds, such as agents that act to neutralize an acidic compound. The therapeutic substances may include a drug, a steroid, an antibiotic, or any other suitable substance that would be apparent to one having ordinary skill in the art in view of the teachings herein. Non-limiting examples of therapeutic substances may include antimicrobial agents, antifungal agents, anti-inflammatory agents, and growth factors. Non-limiting examples of antimicrobial agents include Ionic Silver, Triclosan, Tetracyclines, Doxycycline, Minocycline, Demeclocycline, Tetracycline, Oxytetracycline, Gentamicin, Neomycin, Non-limiting examples of antifungal and antimicrobial agents include Triclosan, Triazole, Thiazole, LAE, Sodium Stearate, Non-limiting examples of anti-inflammatory agents include non-steroidal anti-inflammatory agents (e.g., Salicylates, Aspirin, Diflunisal, Propionic Acid Derivatives, Ibuprofen, Naproxen, Fenoprofen, and Loxoprofen), acetic acid derivatives (e.g., Tolmetin, Sulindac, and Diclofenac), enolic acid derivatives (e.g., Piroxicam, Meloxicam, Droxicam, and Lornoxicam), anthranilic acid derivatives (e.g., Mefenamic Acid, Meclofenamic Acid, and Flufenamic Acid), selective COX-2 inhibitors (e.g., Celecoxib (Celebrex), Parecoxib, Rofecoxib (Vioxx), Sulfonanilides, Nimesulide, and Clonixin), immune selective anti-inflammatory derivatives, corticosteroids (e.g., Dexamethasone), and iNOS inhibitors, Non-limiting examples of growth factors include those that are cell signaling molecules that stimulate cell growth, healing, remodeling, proliferation, and differentiation. Exemplary growth factors can be short-ranged (paracrine), long ranged (endocrine), or self-stimulating (autocrine). Further examples of the growth factors include growth hormones (e.g., a recombinant growth factor, Nutropin, Humatrope, Genotropin, Norditropin, Saizen, Omnitrope, and a biosynthetic growth factor), Epidermal Growth Factor (EGF) (e.g., inhibitors, Gefitinib, Erlotinib, Afatinib, and Cetuximab), heparin-binding EGF like growth factors (e.g., Epiregulin, Betacellulin, Amphiregulin, and Epigen), Transforming Growth Factor alpha (TGF-a), Neuroregulin 1-4, Fibroblast Growth Factors (FGFs) (e.g., FGF1-2, FGF2, FGF11-14, FGF18, FGF15/19, FGF21, FGF23, FGF7 or Keratinocyte Growth Factor (KGF), FGF10 or KGF2, and Phenytoin), Insuline-like Growth Factors (IGFs) (e.g., IGF-1, IGF-2, and Platelet Derived Growth Factor (PDGF)), Vascular Endothelial Growth Factors (VEGFs) (e.g., inhibitors, Bevacizumab, Ranibizumab, VEGF-A, VEGF-B, VEGF-C, VEGF-D and Becaplermin). The therapeutic substances may also include other medicants, such examples may also be further constructed and operable in accordance with at least some of the teachings of U.S. Pub. No. 2017/005986, entitled "Medicant Eluting Adjuncts and Methods of Using Medicant Eluting Adjuncts," published Mar. 2, 2017, issued as U.S. Pat. No. 10,569,071 on Feb. 25, 2020, the disclosure of which is incorporated by reference herein.

Additionally, therapeutic substances may be embedded in a hollow area, such as a porous portion, of valve coupling annular body (712), upper annular flange (714), lower annular flange (716), anchors (718), coiled suture (724), outer weave (720), vertical column-like threads (722), or internal annular sleeve (730). Therapeutic substances may be configured to elute from a portion of the artificial sphincter into the tissue of the biological passageway.

VII. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus configured to be implanted within a biological structure, the apparatus comprising: (a) a plurality of magnetic elements configured to transition the biological structure between an occluded state and an opened state, wherein the plurality of magnetic elements are biased to encourage the biological structure toward the occluded state; (b) an absorbable component comprising a therapeutic substance, wherein the absorbable component is configured to at least temporarily couple the plurality of magnetic elements with the biological structure when the apparatus is initially implanted within the biological structure; and (c) a non-absorbable component.

Example 2

The apparatus of Example 1, wherein the therapeutic substance comprises an anti-inflammatory agent.

Example 3

The apparatus of any one or more of Examples 1 through 2, wherein the therapeutic substance comprises an MMP inhibitor.

Example 4

The apparatus of any one or more or Examples 1 through 3, wherein the absorbable component comprises a plurality of column-like vertical structures configured to promote tissue in-growth.

Example 5

The apparatus of Example 4, wherein the column-like vertical structures are resilient.

Example 6

The apparatus of any one or more of Examples 1 through 5, wherein the non-absorbable component comprises a coiled suture, wherein the coiled suture couples the plurality of magnets and the absorbable component.

Example 7

The apparatus of any one or more of Examples 1 through 6, wherein the therapeutic substance comprises an antibiotic.

Example 8

The apparatus of any one or more of Examples 1 through 7, wherein the therapeutic substance comprises an antimicrobial agent.

Example 9

The apparatus of any one or more of Examples 1 through 8, wherein the absorbable component defines a hollow area, wherein the therapeutic substance is located within the hollow area.

Example 10

The apparatus of Example 9, wherein the therapeutic substance is configured to elute from the absorbable component as the absorbable component absorbs.

Example 11

The apparatus of any one or more of Examples 1 through 10, wherein the therapeutic substance comprises an agent configured to heal tissue.

Example 12

The apparatus of any one or more of Examples 1 through 11, wherein the therapeutic substance comprises an agent configured to physically protect tissue from an acidic compound.

Example 13

The apparatus of any one or more of Examples 1 through 12, wherein the therapeutic substance comprises a steroid.

Example 14

The apparatus of any one or more of Examples 1 through 13, wherein the therapeutic substance comprises a growth factor.

Example 15

The apparatus of any one or more of Examples 1 through 14, wherein the therapeutic substance comprises an antifungal agent.

Example 16

The apparatus of any one or more of Examples 1 through 15, wherein therapeutic substance comprises a drug.

Example 17

An apparatus configured to be implanted within a biological structure, the apparatus comprising: (a) a plurality of magnetic elements configured to transition the biological structure between an occluded state and an opened state, wherein the plurality of magnetic elements are biased to encourage the biological structure toward the occluded state; (b) an absorbable component comprising a therapeutic substance, wherein the absorbable component is configured to contact the biological structure when the apparatus is initially implanted within the biological structure; and (c) a non-absorbable component configured to initially coupled the plurality of magnetic elements with the absorbable component.

Example 18

The apparatus of Example 17, wherein the non-absorbable component comprises a coiled suture.

Example 19

The apparatus of Example 18, wherein the coiled suture wraps around a plurality of through holes defined by the plurality of magnetic elements.

Example 20

An apparatus configured to be implanted within a biological structure, the apparatus comprising: (a) an annular retaining assembly disposed about a central axis, wherein the annular retaining assembly defines an annular opening, wherein the annular retaining assembly comprises: (i) an absorbable ring, wherein the absorbable ring comprises a therapeutic substance, and (ii) a non-absorbable ring; and (b) a plurality of magnets configured to transition the biological structure between an occluded state and an opened state, wherein the plurality of magnetics are biased to encourage the biological structure toward the occluded state.

VIII. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

The teachings herein may be readily combined with the teachings of U.S. Pat. No. 7,175,589, the disclosure of which is incorporated by reference herein; U.S. Pat. No. 7,695,427, the disclosure of which is incorporated by reference herein; U.S. Pat. No. 8,070,670, the disclosure of which is incorporated by reference herein; and/or U.S. Pat. No. 8,734,475, the disclosure of which is incorporated by reference herein. Various suitable ways in which the teachings herein may be combined with the teachings of one or more of the above-cited references will be apparent to those of ordinary skill in the art.

In the examples described herein that include fibrous constructions, absorbable materials, and/or drug eluting capabilities, such examples may further be constructed and operable in accordance with at least some of the teachings of U.S. Pub. No. 2015/0134077, entitled "Sealing Materials for Use in Surgical Stapling," published May 14, 2015, now abandoned, the disclosure of which is incorporated by reference herein. For instance, the teachings of one or more of paragraphs [0103]-[0105], [0110]-[0111], and/or [0127] of U.S. Pub. No. 2015/0134077, now abandoned, may be readily combined with the teachings herein in numerous ways as will be apparent to those of ordinary skill in the art.

In the examples described herein that include absorbable materials and/or drug eluting capabilities, such examples may also be further constructed and operable in accordance with at least some of the teachings of U.S. Pub. No. 2017/0055986, entitled "Medicant Eluting Adjuncts and Methods of Using Medicant Eluting Adjuncts," published Mar. 2, 2017 issued as U.S. Pat. No. 10,569,071 on Feb. 25, 2020, the disclosure of which is incorporated by reference herein. For instance, the teachings of one or more of paragraphs [0389] and/or [0392]-[0402] of U.S. Pub. No. 2017/0055986, issued as U.S. Pat. No. 10,569,071 on Feb. 25, 2020 may be readily combined with the teachings herein in numerous ways as will be apparent to those of ordinary skill in the art.

In the examples described herein that include compressible woven constructs, such examples may further be constructed and operable in accordance with at least some of the teachings of U.S. Pub. No. 2017/0086837, entitled "Compressible Adjunct with Crossing Spacer Fibers," published Mar. 30, 2017, issued as U.S. Pat. No. 10,433,846 on Oct. 8, 2019, the disclosure of which is incorporated by reference herein. For instance, the teachings of one or more of paragraphs [0216]-[0244] may be readily combined with the teachings herein in numerous ways as will be apparent to those of ordinary skill in the art.

In the examples described herein that include absorbable materials and/or materials that promote or discourage tissue in-growth, such examples may further be constructed and operable in accordance with at least some of the teachings of U.S. Pub. No. 2015/0129634, entitled "Tissue Ingrowth Materials and Method of Using the Same," published May 14, 2015, issued as U.S. Pat. No. 9,700,311 on Jul. 11, 2017, the disclosure of which is incorporated by reference herein. For instance, the teachings of one or more of paragraphs [0082]-[0096] of U.S. Pub. No. 2015/0129634, issued as U.S. Pat. No. 9,700,311 on Jul. 11, 2017, may be readily combined with the teachings herein in numerous ways as will be apparent to those of ordinary skill in the art.

In the examples described herein that include absorbable materials and/or materials that promote tissue in-growth, such examples may further be constructed and operable in accordance with at least some of the teachings of U.S. Pub. No. 2015/0133996, entitled "Positively Charged Implantable Materials and Method of Forming the Same," published May 14, 2015, issued as U.S. Pat. No. 10,456,129 on Oct. 29, 2019, the disclosure of which is incorporated by reference herein. For instance, the teachings of one or more of paragraphs [0067]-[0079] of U.S. Pub. No. 2015/0133996, issued as U.S. Pat. No. 10,456,129 on Oct. 20, 2019, may be readily combined with the teachings herein in numerous ways as will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

The teachings presented herein may be further combined with various teachings of any one or more of the following: U.S. application Ser. No. 15/664,464, entitled "An Absorbable Polymer with Drug Elution for a Magnet Sphincter Assist Device," filed on Jul. 31, 2017, published as U.S. Pub. No. 2019/0029794 on Jan. 31, 2019, the disclosure of which is incorporated by reference herein; U.S. application Ser. No. 15/664,566, entitled "Magnet Restraint Mechanism for a Sphincter Assist Device," filed on Jul. 31, 2017, published as U.S. Pub. No. 2019/0029688 on Jan. 31, 2019 the disclosure of which is incorporated by reference herein; U.S. application Ser. No. 15/664,611, entitled "Magnetic Sphincter Replacement Device with Internal Seals," filed on Jul. 31, 2017, published as U.S. Pub. No. 2019/0029795 on Jan. 31, 2019, the disclosure of which is incorporated by reference herein; U.S. application. Ser. No. 15/664,665, entitled "Method for Assisting a Sphincter," filed on Jul. 31, 2017, issued as U.S. Pat. No. 10,405,865 on Sep. 10, 2019, the disclosure of which is incorporated by reference herein; and/or other patents and patent application publications incorporated by reference above.

We claim:

1. An apparatus configured to be implanted within a biological structure, the apparatus comprising:
    (a) a plurality of magnetic elements configured to transition the biological structure between an occluded state and an opened state, wherein the plurality of magnetic elements are biased to encourage the biological structure toward the occluded state;
    (b) an absorbable component comprising a therapeutic substance, wherein the absorbable component is configured to at least temporarily couple the plurality of magnetic elements with the biological structure when the apparatus is initially implanted within the biological structure such that the absorbable component initially supports the plurality of magnetic elements relative to the biological structure; and
    (c) a non-absorbable component.

2. The apparatus of claim 1, wherein the therapeutic substance comprises an anti-inflammatory agent.

3. The apparatus of claim 1, wherein the therapeutic substance comprises an MMP inhibitor.

4. The apparatus of claim 1, wherein the absorbable component comprises a plurality of column-like vertical structures configured to promote tissue in-growth.

5. The apparatus of claim 4, wherein the column-like vertical structures are resilient.

6. The apparatus of claim 1, wherein the non-absorbable component comprises a coiled suture, wherein the coiled suture couples the plurality of magnets and the absorbable component.

7. The apparatus of 1, wherein the therapeutic substance comprises an antibiotic.

8. The apparatus of claim 1, wherein the therapeutic substance comprises an antimicrobial agent.

9. The apparatus of claim 1, wherein the absorbable component defines a hollow area, wherein the therapeutic substance is located within the hollow area.

10. The apparatus of claim 8, wherein the therapeutic substance is configured to elute from the absorbable component as the absorbable component absorbs.

11. The apparatus of claim 1, wherein the therapeutic substance comprises an agent configured to heal tissue.

12. The apparatus of claim 1, wherein the therapeutic substance comprises an agent configured to physically protect tissue from an acidic compound.

13. The apparatus of claim 1, wherein the therapeutic substance comprises a steroid.

14. The apparatus of claim 1, wherein the therapeutic substance comprises a growth factor.

15. The apparatus of claim 1, wherein the therapeutic substance comprises an antifungal agent.

16. The apparatus of claim 1, wherein therapeutic substance comprises a drug.

17. An apparatus configured to be implanted within a biological structure, the apparatus comprising:
(a) a plurality of magnetic elements configured to transition the biological structure between an occluded state and an opened state, wherein the plurality of magnetic elements are biased to encourage the biological structure toward the occluded state, wherein the plurality of magnetic elements are disposed about a central axis;
(b) an absorbable component comprising a therapeutic substance, wherein the plurality of magnetic elements are disposed between the absorbable component and the central axis, wherein the therapeutic substance is configured to at least temporarily support the plurality of magnetic elements relative to the biological structure when the apparatus is initially implanted within the biological structure; and
(c) a non-absorbable component configured to support the plurality of magnetic elements relative to the biological structure after the absorbable component is bio-absorbed.

18. The apparatus of claim 17, wherein the apparatus comprises a silicone bag, wherein the plurality of magnetic elements are disposed within the silicone bag.

19. An apparatus configured to be implanted within a biological structure, the apparatus comprising:
(a) a plurality of magnetic elements disposed about a central axis configured to transition the biological structure between an occluded state and an opened state, wherein the plurality of magnetic elements are biased to encourage the biological structure toward the occluded state;
(b) an absorbable component located further away from the central axis compared to the plurality of magnetic elements, wherein the absorbable component comprises a therapeutic substance, wherein the absorbable component is configured to at least temporarily couple the plurality of magnetic elements with the biological structure when the apparatus is initially implanted within the biological structure; and
(c) a non-absorbable component.

20. The apparatus of claim 19, wherein the non-absorbable component comprises a coil disposed around the plurality of magnetic elements.

* * * * *